US011771958B2

United States Patent
Takagi et al.

(10) Patent No.: US 11,771,958 B2
(45) Date of Patent: Oct. 3, 2023

(54) INSTRUCTING PROCESS MANAGEMENT SYSTEM FOR TREATMENT AND/OR EXERCISE, AND PROGRAM, COMPUTER APPARATUS AND METHOD FOR MANAGING INSTRUCTING PROCESS FOR TREATMENT AND/OR EXERCISE

(71) Applicant: Rika Takagi, Aichi (JP)

(72) Inventors: Rika Takagi, Aichi (JP); Hisayoshi Yoshitake, Aichi (JP); Toshimitsu Ishizuka, Kanagawa (JP)

(73) Assignee: Rika Takagi, Aichi (JP)

( * ) Notice: Subject to any disclaimer, the term of this patent is extended or adjusted under 35 U.S.C. 154(b) by 673 days.

(21) Appl. No.: 16/627,479

(22) PCT Filed: Jul. 7, 2017

(86) PCT No.: PCT/JP2017/025042
§ 371 (c)(1),
(2) Date: Dec. 30, 2019

(87) PCT Pub. No.: WO2019/008771
PCT Pub. Date: Jan. 10, 2019

(65) Prior Publication Data
US 2020/0155900 A1 May 21, 2020

(51) Int. Cl.
*G06V 40/20* (2022.01)
*G16H 20/30* (2018.01)
(Continued)

(52) U.S. Cl.
CPC ...... *A63B 24/0062* (2013.01); *A63B 24/0003* (2013.01); *G06F 3/0482* (2013.01);
(Continued)

(58) Field of Classification Search
CPC ............ A63B 24/0062; A63B 24/0003; A63B 2024/0071; A63B 69/00; A63B 71/00;
(Continued)

(56) References Cited

U.S. PATENT DOCUMENTS 9,072,929 B1 * 7/2015 Rush .................... H04N 13/257
9,870,622 B1 * 1/2018 Lu ........................... G06T 7/251
(Continued)

FOREIGN PATENT DOCUMENTS

JP     10-263126     10/1998
JP     2003-256568     9/2003
(Continued)

OTHER PUBLICATIONS

International Search Report issued in International Patent Application No. PCT/JP2017/025042, dated Sep. 19, 2017 with an English translation thereof.
(Continued)

*Primary Examiner* — Sundhara M Ganesan
(74) *Attorney, Agent, or Firm* — GREENBLUM & BERNSTEIN, P.L.C.

(57) ABSTRACT

The present invention achieves a therapy and/or exercise instructing process management that is capable of providing an exercise menu sufficiently suited for an exerciser by considering the state of the body of the exerciser. The above object is achieved to provide a therapy and/or exercise instructing process management system implemented by a client-side terminal operated by a client and a trainer-side terminal that is connectable to the client-side terminal via communication and operated by a trainer, the system including: an assessor that assesses a posture of the client in a steady state and/or a moving state; an exercise determiner that determines exercise to be performed by the client based on an assessment made by the assessor; and a storage that
(Continued)

stores information regarding the assessment made by the assessor and information regarding the exercise that is determined by the exercise determiner and performed by the client.

14 Claims, 12 Drawing Sheets

(51) Int. Cl.
*A63B 24/00* (2006.01)
*G06F 3/0482* (2013.01)
*G06F 3/04883* (2022.01)
*G06V 40/00* (2022.01)

(52) U.S. Cl.
CPC .......... *G06F 3/04883* (2013.01); *G06V 40/00* (2022.01); *G06V 40/23* (2022.01); *G16H 20/30* (2018.01); *A63B 2024/0071* (2013.01); *G01N 2800/2842* (2013.01)

(58) Field of Classification Search
CPC ... A63B 71/06; G06F 3/0482; G06F 3/04883; G06V 40/00; G06V 40/23; G01N 2800/2842; A61B 5/107; A61H 99/00; G16H 20/30
See application file for complete search history.

(56) References Cited

U.S. PATENT DOCUMENTS

| | | | |
|---|---|---|---|
| 10,213,645 B1* | 2/2019 | Wu | G06K 9/6277 |
| 10,262,079 B1* | 4/2019 | Costabello | G16H 20/30 |
| 10,835,802 B1* | 11/2020 | Mayer | G06F 3/015 |
| 10,894,198 B1* | 1/2021 | Teeger | A63B 71/0605 |
| 2005/0182341 A1 | 8/2005 | Katayama et al. | |
| 2009/0125333 A1 | 5/2009 | Heywood et al. | |
| 2009/0299232 A1* | 12/2009 | Lanfermann | A61B 5/1122 600/595 |
| 2010/0048358 A1* | 2/2010 | Tchao | G06F 3/016 482/8 |
| 2010/0177933 A1* | 7/2010 | Willmann | G06T 7/0012 382/107 |
| 2010/0306712 A1* | 12/2010 | Snook | G16H 20/30 715/863 |
| 2012/0000300 A1 | 1/2012 | Sunagawa et al. | |
| 2012/0253489 A1* | 10/2012 | Dugan | G06V 40/23 700/91 |
| 2012/0268592 A1* | 10/2012 | Aragones | A61B 5/1118 702/19 |
| 2013/0102439 A1* | 4/2013 | Napolitano | A61B 5/1113 482/8 |
| 2013/0120445 A1* | 5/2013 | Shimomura | G02B 27/017 345/629 |
| 2013/0123667 A1* | 5/2013 | Komatireddy | A61B 5/746 600/595 |
| 2013/0171601 A1* | 7/2013 | Yuasa | G06V 40/23 434/258 |
| 2013/0172154 A1* | 7/2013 | Kim | A61B 5/222 482/8 |
| 2013/0223707 A1* | 8/2013 | Stephenson | A61B 5/1124 382/128 |
| 2014/0093856 A1 | 4/2014 | Watanabe et al. | |
| 2014/0147820 A1* | 5/2014 | Snow | G09B 19/0038 434/247 |
| 2014/0174174 A1* | 6/2014 | Uehara | A61B 5/227 700/91 |
| 2014/0267611 A1* | 9/2014 | Kennett | G06V 40/20 348/46 |
| 2015/0039106 A1* | 2/2015 | Bonstrom | G06V 40/23 700/91 |
| 2015/0099252 A1* | 4/2015 | Anderson | G06T 7/251 434/257 |
| 2015/0151199 A1* | 6/2015 | Klein | A63F 13/213 463/7 |
| 2015/0202510 A1* | 7/2015 | Appleton | G09B 19/0038 473/446 |
| 2015/0294481 A1* | 10/2015 | Sakaue | G06V 40/23 600/595 |
| 2015/0310629 A1* | 10/2015 | Utsunomiya | G06T 7/246 382/107 |
| 2015/0324637 A1* | 11/2015 | Utsunomiya | G16H 20/70 382/107 |
| 2015/0325270 A1* | 11/2015 | Utsunomiya | G06V 40/25 386/230 |
| 2015/0339854 A1* | 11/2015 | Adler | G16H 20/30 345/419 |
| 2015/0375039 A1* | 12/2015 | Park | G16H 20/30 482/8 |
| 2016/0008661 A1* | 1/2016 | Ferro Bento | G16H 20/30 702/150 |
| 2016/0027325 A1* | 1/2016 | Malhotra | G16H 30/40 434/247 |
| 2016/0059073 A1* | 3/2016 | Jeon | G06Q 30/0241 482/8 |
| 2016/0059103 A1* | 3/2016 | Han | G06Q 10/0639 700/91 |
| 2016/0071284 A1* | 3/2016 | Kontschieder | G06N 20/00 382/107 |
| 2016/0151672 A1* | 6/2016 | Barnes | G06V 40/23 434/247 |
| 2016/0175650 A1* | 6/2016 | Sato | G16H 20/30 702/151 |
| 2016/0216770 A1* | 7/2016 | Jang | G06F 3/017 |
| 2016/0263439 A1* | 9/2016 | Ackland | A61B 5/0205 |
| 2016/0346584 A1* | 12/2016 | Schneider | H01L 27/16 |
| 2017/0036082 A1* | 2/2017 | Kodaira | A63B 60/46 |
| 2017/0043217 A1* | 2/2017 | Lee | G06V 40/23 |
| 2017/0046052 A1* | 2/2017 | Lee | G16H 20/60 |
| 2017/0084070 A1* | 3/2017 | Chamdani | G09B 19/0038 |
| 2017/0100630 A1* | 4/2017 | Mizuno | A63B 23/12 |
| 2017/0100637 A1* | 4/2017 | Princen | G16H 20/30 |
| 2017/0136296 A1* | 5/2017 | Barrera | G16H 20/30 |
| 2017/0189784 A1* | 7/2017 | Sasaki | G09B 19/003 |
| 2017/0232324 A1* | 8/2017 | Mettler May | G06V 40/20 473/459 |
| 2017/0239523 A1* | 8/2017 | Cheng | G06V 10/17 |
| 2017/0345332 A1* | 11/2017 | Obay | A61B 5/6895 |
| 2017/0354845 A1* | 12/2017 | Williams | G06F 3/0481 |
| 2017/0365048 A1* | 12/2017 | Hamilton, II | G16Z 99/00 |
| 2018/0021653 A1* | 1/2018 | Thornbrue | G01C 21/16 473/453 |
| 2018/0049937 A1* | 2/2018 | Fauquex | A61H 1/0255 |
| 2018/0053349 A1* | 2/2018 | Chen | G06T 19/006 |
| 2018/0065025 A1* | 3/2018 | Toda | G16H 20/30 |
| 2018/0104541 A1* | 4/2018 | Katis, Jr. | A63B 71/0622 |
| 2018/0117446 A1* | 5/2018 | Tran | A42B 3/0433 |
| 2018/0117447 A1* | 5/2018 | Tran | G06Q 20/382 |
| 2018/0121728 A1* | 5/2018 | Wells | G02B 27/0176 |
| 2018/0188284 A1* | 7/2018 | Douglas | G06F 3/04847 |
| 2018/0199861 A1* | 7/2018 | Ye | G16H 20/30 |
| 2018/0264322 A1* | 9/2018 | Yoshihama | H04Q 9/00 |
| 2018/0264347 A1* | 9/2018 | Tran | A63B 43/004 |
| 2018/0311561 A1* | 11/2018 | Puzhevich | G09B 19/0038 |
| 2018/0315247 A1* | 11/2018 | Van Andel | G16H 20/30 |
| 2018/0318645 A1* | 11/2018 | Shin | H04L 67/535 |
| 2018/0338710 A1* | 11/2018 | Tas | A61B 5/7246 |
| 2019/0156934 A1* | 5/2019 | Kataoka | G07C 5/0816 |
| 2019/0175078 A1* | 6/2019 | Chen | A61B 5/6802 |
| 2019/0176043 A1* | 6/2019 | Gosine | A61B 5/1114 |
| 2019/0206568 A1* | 7/2019 | Clark | G16H 50/20 |
| 2019/0275373 A1* | 9/2019 | Takatsuka | G06Q 30/02 |
| 2019/0362139 A1* | 11/2019 | Mehl | A61B 5/486 |
| 2020/0054928 A1* | 2/2020 | Ananth | G06V 40/23 |
| 2020/0155900 A1* | 5/2020 | Takagi | G06F 3/0482 |
| 2020/0211411 A1* | 7/2020 | Katz | G06V 20/20 |
| 2020/0237264 A1* | 7/2020 | Kimura | G16H 40/63 |
| 2020/0246660 A1* | 8/2020 | Kim | A61B 5/1128 |

(56) References Cited

U.S. PATENT DOCUMENTS

2020/0384313 A1* 12/2020 Singh ............... G16H 50/50
2020/0402638 A1* 12/2020 Song ............... A63B 24/0087

FOREIGN PATENT DOCUMENTS

| JP | 2005-000301 | 1/2005 |
| JP | 2005-224452 | 8/2005 |
| JP | 2007-334381 | 12/2007 |
| JP | 2008-178605 | 8/2008 |
| JP | 201178728 | 4/2011 |
| JP | 2013-066672 | 4/2013 |
| JP | 2014-068760 | 4/2014 |
| JP | 2014-078145 | 5/2014 |
| JP | 2015-064914 | 4/2015 |
| JP | 2016/019695 | 2/2016 |
| JP | 2016-073789 | 5/2016 |
| WO | 2013/078208 | 5/2013 |

OTHER PUBLICATIONS

Written Opinion of the International Searching Authority issued in International Application No. PCT/JP2017/025042, dated Sep. 19, 2017 with an English translation thereof.

Official communication issued in Japanese Patent Application No. JP2019-528328, dated Jan. 5, 2021 with an English translation thereof.

Official communication issued in Japanese Patent Application No. JP2021-069323, dated Feb. 8, 2022 with an English translation thereof.

Official communication issued in Japanese Patent Application No. JP2021-069323, dated Apr. 26, 2022 with an English translation thereof.

* cited by examiner

FIG. 12

| SYMPTOM SITE | SYMPTOM TYPE | SYMPTOM LEVEL | POSTURE PATTERN | EXERCISE MENU |
|---|---|---|---|---|
| N/A | N/A | N/A | PATTERN A-1 | EXERCISE MENU A1 | ... |
| N/A | N/A | N/A | PATTERN A-2 | EXERCISE MENU A2 | ... |
| N/A | N/A | ... | ... | ... | ... |
| N/A | N/A | N/A | PATTERN B-1 | EXERCISE MENU B1 | ... |
| ... | ... | ... | ... | ... | ... |
| LEFT SHOULDER | PAIN (AFTER EXERCISING) | 1~3 | PATTERN A-1 | EXERCISE MENU A11 | ... |
| LEFT SHOULDER | PAIN (AFTER EXERCISING) | 1~3 | PATTERN A-2 | EXERCISE MENU A12 | ... |
| ... | ... | ... | ... | ... | ... |
| LEFT SHOULDER | PAIN (AFTER EXERCISING) | 4~7 | PATTERN A-1 | EXERCISE MENU A21 | ... |
| ... | ... | ... | ... | ... | ... |

502  503  504  505  506

501

INSTRUCTING PROCESS MANAGEMENT SYSTEM FOR TREATMENT AND/OR EXERCISE, AND PROGRAM, COMPUTER APPARATUS AND METHOD FOR MANAGING INSTRUCTING PROCESS FOR TREATMENT AND/OR EXERCISE

TECHNICAL FIELD

The present invention relates to a therapy and/or exercise instructing process management system and to a program, a computer apparatus, and a method for performing therapy and/or exercise instructing process management.

BACKGROUND ART

Recently, an increasing number of people do exercise by utilizing training facilities in order to increase one's motor functions. In such a training facility, normally, there is an instructor who gives advice to the users of the facility regarding exercise, so that the users can receive the advice from the instructor regarding what kind of exercise menu to perform for increasing the motor function for the purpose of the user. However, there may be a situation where the user is not able to receive such advice when the instructor is giving advice to another user, for example. In such case, it is difficult for the user to grasp what kind of exercise menu to perform for the user's purpose.

In order to overcome such a problem, for example, Patent Literature 1 proposes a support system which, by using a terminal apparatus placed within a training facility, receives input from a user regarding the purpose of training, and presents an exercise menu suited for the purpose of the training.

Incidentally, in therapeutic facilities such as an osteopathic clinic, a chiropractic clinic, and a rehabilitation facility, so-called exercise therapy is performed with which symptoms of a patient can be lightened or cured or the functions can be recovered by encouraging the patient to do various kinds of exercise. While the exercise therapy is considered effective means even for treatment of diabetes and the like, a sufficient effect cannot be acquired with the exercise therapy when the patient does not properly perform the exercise.

In order to overcome such problem, for example, Patent Literature 2 proposes an exercise support system which assesses whether or not exercise of a patient is performed properly based on an analysis result of a video that is acquired by capturing a state of the patient doing the exercise and based on a surface electromyogram acquired by electromyography.

CITATION LIST

Patent Literature

Patent Literature 1: JP 2014-68760 A
Patent Literature 2: JP 2016-19695 A

SUMMARY OF INVENTION

Technical Problem

However, even though the support system disclosed in Patent Literature 1 presents the exercise menu suited for the purpose of the training of the user, there is no consideration taken over the body condition of the user. Therefore, even when the exercise menu is effective for a specific purpose of training, it is not necessarily effective for that user and a sufficient effect cannot be acquired when it is not effective for the user. For example, when the state and the like of the trunk and other muscles of the user are not in a suitable state for performing the exercise menu, muscles that are not supposed to be used may be used or excessive load may be imposed upon joints and soft tissues in the periphery of the joints when performing the exercise menu, which may rather cause damages or general malaise.

Similarly, while the exercise support system disclosed in Patent Literature 2 assesses whether or not the exercise of the patient is performed properly and encourages the patient to do the exercise with proper motions so as to increase the effect of the exercise, it is not possible to acquire a sufficient effect when the exercise menu itself is not appropriate for the patient. Even when the exercise menu is effective for a specific symptom, it is not necessarily effective for that patient. For example, when the state and the like of the trunk and other muscles of the patient are not in a suitable state for performing the exercise menu, damages or general malaise may rather be caused.

Further, in general, exercise menus for the patients and the exercisers such as the users of training facilities may be determined in many cases by exercise directors such as a judo therapist, a physical therapist, and an instructor by considering the symptoms of the patients and the purposes of the users. In that case, even if the exercise directors determine the exercise menu by considering not only the symptoms and the purpose of the exerciser but also the state of the trunk and other muscles of the exerciser, the efficiency of the exercise menu varies depending on the knowledges and experiences of the exercise directors. It is difficult for the exercise director without sufficient knowledge and experience to make appropriate decision on the body condition of the exerciser, so that the exercise menu determined by such exercise director tends to have low efficiency. That is, in conventional exercise instructions, the exercise menu given to the exercisers may become an exercise menu determined without considering the state of the trunk and other muscles of the exerciser or may become an exercise menu determined without making proper decision on the state of the trunk and other muscles of the exerciser, for example. Therefore, the efficiency thereof depends on the individual skills of the exercise director, so that it is not considered that the efficiency is sufficiently secured.

The present invention is designed in view of the aforementioned problems. That is, the first object of the present invention is to achieve therapy and/or exercise instructing process management that is capable of providing an exercise menu sufficiently suited for an exerciser by considering the state of the body of the exerciser. Further, the second object of the present invention is to achieve therapy and/or exercise instructing process management that is capable of providing an exercise menu with a certain level of efficiency or more secured by suppressing differences in individual skills when determining the exercise menu.

Solution to Problem

The present invention is summarized as follows.

[1] A therapy and/or exercise instructing process management system implemented by a client-side terminal operated by a client and a trainer-side terminal that is connectable to the client-side terminal via communication and operated by a trainer, the system including: an assessor that assesses a posture of the client in a steady state and/or a moving state;

an exercise determiner that determines exercise to be performed by the client based on an assessment made by the assessor; and a storage that stores information regarding the assessment made by the assessor and information regarding the exercise that is determined by the exercise determiner and performed by the client.

[2] The therapy and/or exercise instructing process management system according to above [1], further including a displayer that is capable of displaying at least a part of the information stored in the storage on the client-side terminal and the trainer-side terminal.

[3] The therapy and/or exercise instructing process management system according to above [2], wherein the displayer further displays an ideal target image showing a posture to be a target of the client, the ideal target image corresponding to the posture of the client in the steady state and/or the moving state assessed by the assessor.

[4] The therapy and/or exercise instructing process management system according to above [2] or [3], wherein the displayer further displays an unideal target image showing a posture that is not supposed to be a target of the client, the unideal target image having in common at least a part of factors not satisfying a prescribed assessment criteria in the posture of the client, and corresponding to the posture of the client in the steady state and/or the moving state assessed by the assessor.

[5] The therapy and/or exercise instructing process management system according to any one of above [2] to [4], wherein: the storage stores the information regarding the assessment in association with date or time and date on which the assessment is made, and stores the information regarding the exercise performed by the client in association with date or time and date on which the exercise is performed; and the displayer is capable of displaying at least a part of the information stored in the storage in chronological order.

[6] The therapy and/or exercise instructing process management system according to any one of above [2] to [5], further including an inputter that inputs a site having a prescribed symptom in a body of the client, a type of the symptom of the site, and a level of the symptom of the site, wherein the displayer displays information indicating the type of the symptom of the site and the level of the symptom of the site at a position corresponding to the site having the prescribed symptom on a drawing regarding an external appearance of the body.

[7] The therapy and/or exercise instructing process management system according to any one of above [2] to [6], further including a posting receiver that receives a posting of a message and/or an image from the client-side terminal and the trainer-side terminal, wherein the displayer further displays the message and/or the image received by the posting receiver on the client-side terminal and the trainer-side terminal.

[8] The therapy and/or exercise instructing process management system according to above [7], further including an image capturer capable of capturing an image of the client, wherein the posting receiver is capable of receiving a posting of an image of the exercise that is performed by the client and captured by the image capturer.

[9] The therapy and/or exercise instructing process management system according to any one of above [1] to [8], further including an image capturer capable of capturing an image of the client, wherein the assessor assesses the posture of the client in the steady state and/or the moving state based on the image captured by the image capturer.

[10] The therapy and/or exercise instructing process management system according to above [9], wherein the assessor assesses the posture based on a position of a prescribed body site of the client, an inclination of the prescribed body site of the client, and/or positional relationships among a plurality of prescribed body sites in the image captured by the image capturer.

[11] The therapy and/or exercise instructing process management system according to above [9] or [10], further including an object drawer that draws a plurality of objects for visualizing positions and/or inclinations of each of prescribed body sites of the client in the image captured by the image capturer, wherein the assessor assess the posture based on the positions of the objects, the inclinations of the prescribed body site of the client, and positional relationships among the plurality of objects.

[12] A program causing a computer apparatus to execute therapy and/or exercise instructing process management, the program causing the computer apparatus to function as: an assessor that assesses a posture of a client in a steady state and/or a moving state; an exercise determiner that determines exercise to be performed by the client based on an assessment made by the assessor; and a storage that stores information regarding the assessment made by the assessor and information regarding the exercise that is determined by the exercise determiner and performed by the client.

[13] A computer apparatus executing therapy and/or exercise instructing process management, including: an assessor that assesses a posture of a client in a steady state and/or a moving state; an exercise determiner that determines exercise to be performed by the client based on an assessment made by the assessor; and a storage that stores information regarding the assessment made by the assessor and information regarding the exercise that is determined by the exercise determiner and performed by the client.

[14] A therapy and/or exercise instructing process management method, including: a step of assessing a posture of a client in a steady state and/or a moving state; a step of determining exercise to be performed by the client based on an assessment made in the step of assessing; and a step of storing, in a computer apparatus, information regarding the assessment made in the step of assessing and information regarding the exercise that is determined in the step of determining exercise and performed by the client.

Advantageous Effects of Invention

With the present invention, it is possible to provide the exercise menu that is sufficiently suited for the client while considering the state of the body of the client by assessing the posture of the client in a steady state and/or moving state and determining the exercise to be performed by the client based on the assessment. Further, with the present invention having such the configuration described above, it is possible to provide the exercise menu with a certain level of efficiency or more secured by suppressing differences in individual skills when determining the exercise menu.

BRIEF DESCRIPTION OF THE DRAWINGS

FIG. 12 is an example of a master table that corresponds to at least one of the embodiments of the present invention.

DESCRIPTION OF EMBODIMENTS

Figure 1:
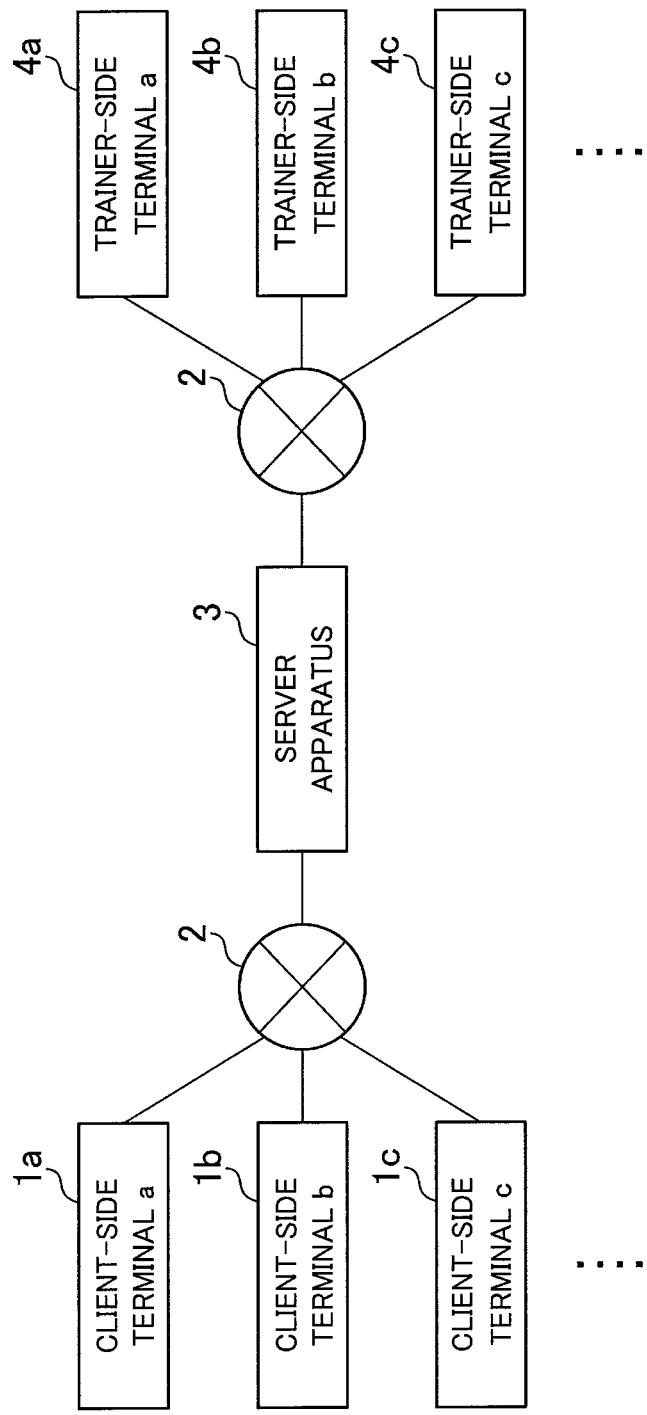
FIG. 1 is a diagram illustrating a configuration of the therapy and/or exercise instructing process management system corresponding to at least one of the embodiments of the present invention.

While embodiments of the present invention will be described with reference to the accompanying drawings and the like hereinafter, the present invention is not limited to the following embodiments without departing from the purpose of the present invention. In the drawings, different numeral signs may be applied even to the same sites of human bodies. Further, the sequential order of each processing constituting flowcharts described in the Description is a random order within a range where there is no confliction or inconsistency generated in the processing contents.

In the Description, a "client" means a person who performs exercise, and examples thereof may be users of training facilities, sports enthusiasts, athletes, and patients performing exercise therapies. Further, a "trainer" means a person who gives instructions and advices regarding the exercise for the client, and examples thereof may be instructors of training facilities, sport trainers, coaches, judo therapists, and physical therapists. Furthermore, an "image" may be a still image or a video.

First Embodiment

First, outline of the first embodiment of the present invention will be described. As the first embodiment, described is a therapy and/or exercise instructing process management system that is implemented by: a client-side terminal operated by a client; and a trainer-side terminal that is connectable to the client-side terminal via communication and operated by a trainer.

FIG. 1 is a diagram illustrating a configuration of the therapy and/or exercise instructing process management system corresponding to at least one of the embodiments of the present invention. As illustrated, the therapy and/or exercise instructing process management system is configured with: a plurality of client-side terminals 1 (client-side terminals 1a, 1b, 1c, . . . ); a communication network 2; a server apparatus 3; and a plurality of trainer-side terminals 4 (trainer-side terminals 4a, 4b, 4c, . . . ).

The client-side terminal 1 is connected to the server apparatus 3 via the communication network 2. The trainer-side terminal 4 is connected to the server apparatus 3 via the communication network 2. The server apparatus 3 may not have to be constantly connected to the client-side terminal 1 and the trainer-side terminal 4 but may only need to be connectable to each of the terminals as necessary. While the client-side terminals 1 and the trainer-side terminals 4 are communicably connected to the communication network 2 via the server apparatus 3 in the configuration illustrated in FIG. 1, those terminals may be communicably connected without having the server apparatus 3 interposed therebetween. That is, there may be no server apparatus 3.

The client-side terminal 1 is a terminal to be operated by a client. While not limited thereto, examples of the client-side terminal 1 may be a personal computer, a smartphone, a tablet terminal, a mobile phone, a PDA, and the like. The client-side terminal 1 may be an apparatus that is connectable to the server apparatus 3 or the trainer-side terminal 4 via the communication network 2.

As the communication network 2, for example, it is possible to use various kinds of wired or wireless known communication networks such as the Internet, wired or wireless public telephone network, wired or wireless LAN, and a dedicated line.

The server apparatus 3 is a management/operation server that includes: a function of transmitting and receiving information between the client-side terminal 1 and the trainer-side terminal 4; a function of storing and managing the information received from the client-side terminal 1 and the trainer-side terminal 4; and the like.

The trainer-side terminal 4 is a terminal to be operated by a trainer. While not limited to thereto, examples of the trainer-side terminal 4 may be a personal computer, a smartphone, a tablet terminal, a mobile phone, and a PDA. The trainer-side terminal 4 may be an apparatus that is connectable to the server apparatus 3 or the client-side terminal 1 via the communication network 2.

Figure 2:
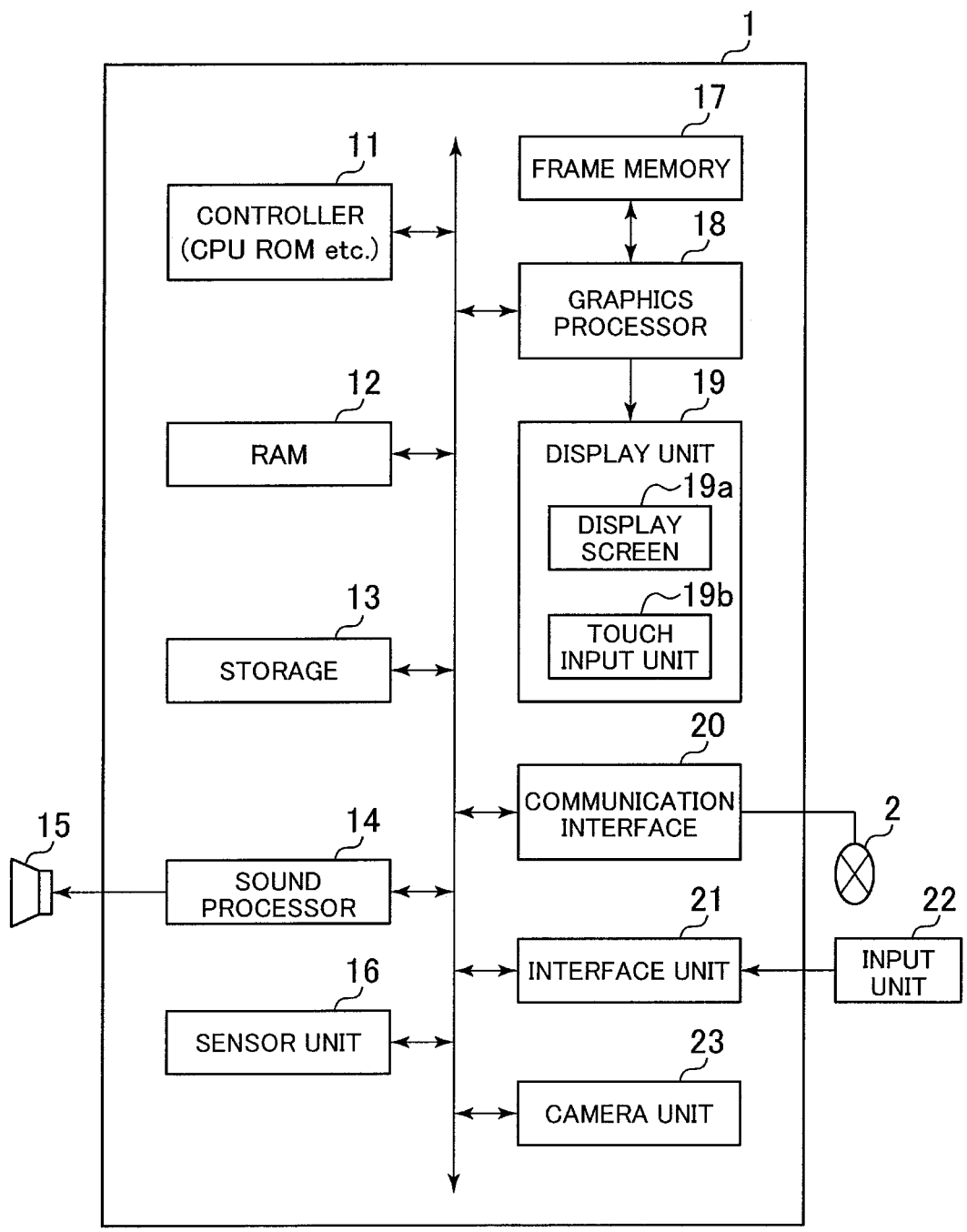
FIG. 2 is a block diagram illustrating a configuration of the client-side terminal corresponding to at least one of the embodiments of the present invention.

FIG. 2 is a block diagram illustrating a configuration of the client-side terminal corresponding to at least one of the embodiments of the present invention. The client-side terminal 1 includes at least a controller 11, a RAM (Random Access Memory) 12, a storage 13, a sound processor 14, a sensor unit 16, a graphics processor 18, a display unit 19, a communication interface 20, an interface unit 21, and a camera unit 23, and each of those is connected via an internal bus.

The controller 11 is configured with a CPU (Central Processor) and a ROM (Read Only Memory), and includes an internal timer for clocking the time. The controller 11 executes programs stored in the storage 13 and controls the client-side terminal 1. The RAM 12 is a work area of the controller 11. The storage 13 is a memory area for saving the programs and data.

The controller 11 reads out the program and data from the RAM 12 and performs processing. The controller 11 processes the program and the data loaded on the RAM 12 to output an instruction to output sound to the sound processor 14 and to output an image drawing command to the graphics processor 18.

The sound processor 14 is connected to a sound output apparatus 15 that is a speaker. When the controller 11 outputs an instruction of sound output to the sound processor 14, the sound processor 14 outputs a sound signal to the sound output apparatus 15. It is preferable to output instructions of exercise contents and feedback regarding the exercise, for example, from the sound output apparatus 15 with voice.

The sensor unit 16 includes at least one or more sensor selected from a group consisting of a depth sensor, an accelerometer, a gyro sensor, a GPS sensor, a fingerprint authentication sensor, a proximity sensor, a magnetic sensor, a luminance sensor, a GPS sensor, and a barometric pressure sensor. In view of monitoring in detail the state of the exercise performed by the client, it is preferable for the sensor unit 16 to include the depth sensor, for example. Note that, in order to monitor in detail the state of the exercise performed by the client, an external apparatus such as a motion capture apparatus, a pressure sensor, electromyography, or an ultrasonic measurement device may be used, and the information from the external apparatus may be received at the client-side terminal 1.

The graphics processor 18 is connected to the display unit 19. The display unit 19 includes a display screen 19a and a touch input unit 19b. When the controller 11 outputs an image drawing command to the graphics processor 18, the graphics processor 18 develops an image on a frame memory (frame buffer) 17, and outputs a video signal for displaying the image on the display screen 19a. The touch input unit 19b receives operation input of the client, senses a pressure on the touch input unit 19b applied by a finger, a stylus, or the like and shift of the position of the finger or the like, and detects a change and the like of the coordinate position. The display screen 19a and the touch input unit 19b may also be configured integrally like a touch panel, for example.

The graphics processor 18 executes drawing of a single image by a frame unit. One frame time of the image is 1/30 seconds, for example. The graphics processor 18 has a role of dispersing the load of the entire system by undertaking a part of calculation processing regarding drawing the image that is used to be carried out by the controller 11 alone.

The communication interface 20 is capable of connecting to the communication network 2 wirelessly or with wire, and capable of transmitting/receiving data via the communication network 2. The data received via the communication network 2 is loaded on the RAM 12, and calculation processing is performed by the controller 11.

An input unit 22 (for example, a mouse or a keyboard) can be connected to the interface unit 21. Input information inputted by the client through the input unit 22 is stored in the RAM 12, and the controller 11 executes various kinds of calculation processing based on the input information. Alternatively, it is also possible to connect a storage medium reader to the interface unit 21, and load the program, the data, and the like from an external memory or the like. Further, it is also possible to use the display unit 19 provided with a touch panel as the input unit 22.

The camera unit 23 is for capturing images of the client, and captures the postures of the client in a steady state and/or moving state and the state where the client is performing the exercise, for example. The image captured by the camera unit 23 is outputted to the graphics processor 18. Note that the camera unit 23 may not be provided to the client-side terminal 1. For example, the captured images of the client may be acquired by fetching images captured by an external image capturing apparatus.

Figure 3:
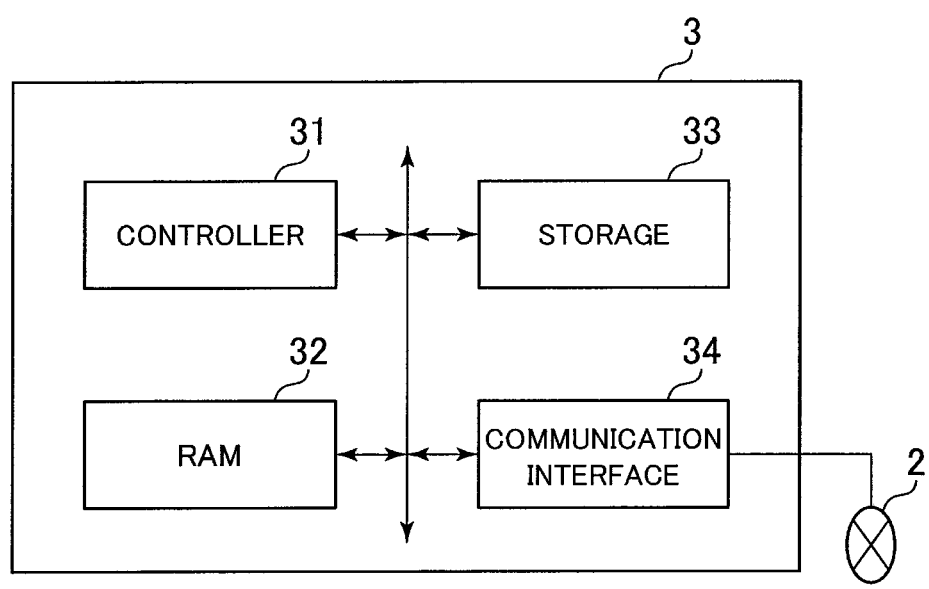
FIG. 3 is a block diagram illustrating a configuration of the server apparatus corresponding to at least one of the embodiments of the present invention.

FIG. 3 is a block diagram illustrating a configuration of the server apparatus corresponding to at least one of the embodiments of the present invention. The server apparatus 3 includes at least a controller 31, a RAM 32, a storage 33, and a communication interface 34, and each thereof is connected via an internal bus.

The controller 31 is configured with a CPU and a ROM, and includes an internal timer for clocking the time. The controller 31 executes programs stored in the storage 33, and controls the server apparatus 3. The RAM 32 is a work area of the controller 31. The storage 33 is a memory area for saving the programs and data. The controller 31 reads out the programs and data from the RAM 12 and performs program execution processing based on the information and the like received from the client-side terminal 1.

The communication interface 34 is capable of connecting to the communication network 2 wirelessly or with wire, and capable of transmitting/receiving data via the communication network 2. The data received via the communication network 2 is loaded on the RAM 32, and calculation processing is performed by the controller 31, for example.

Figure 4:
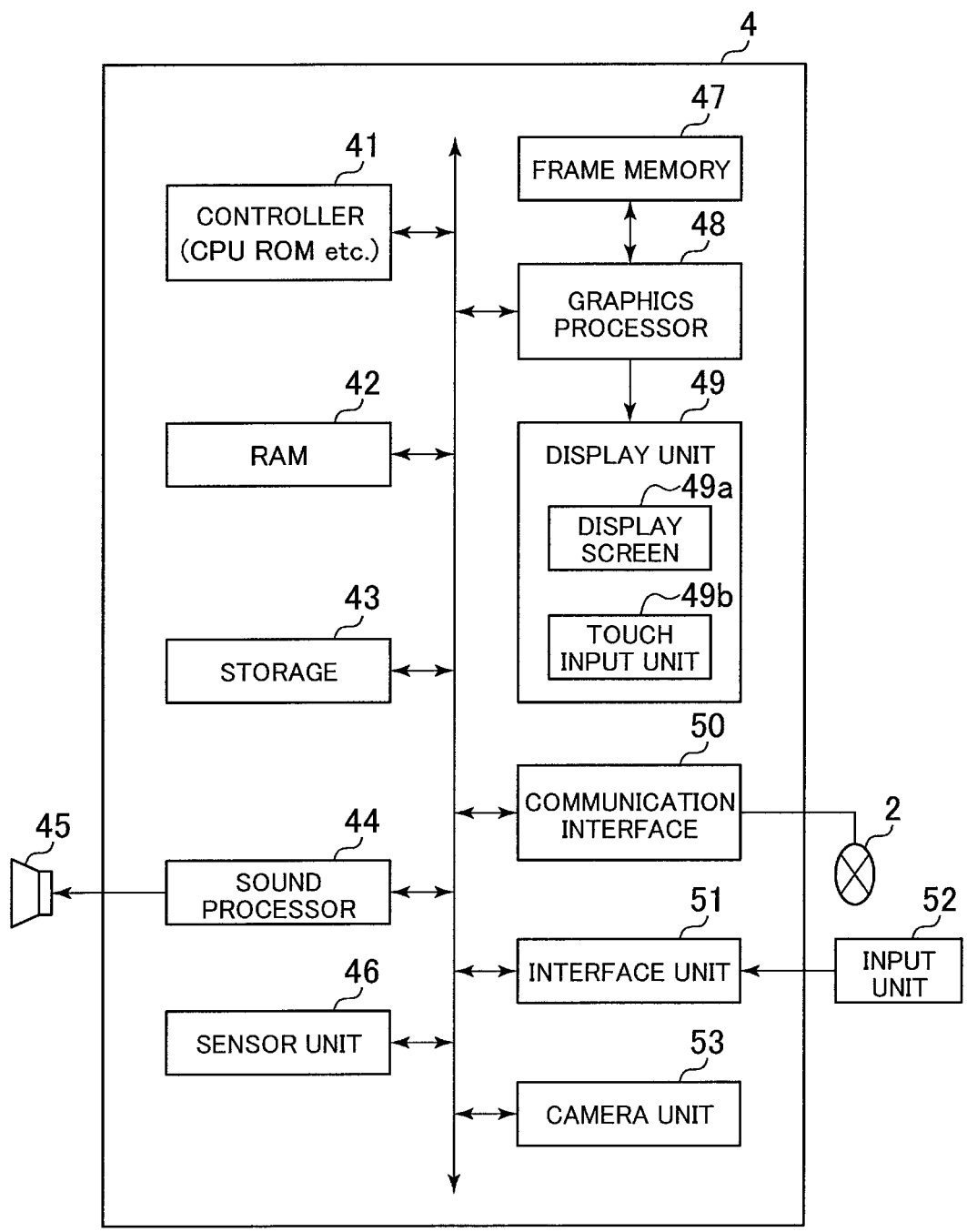
FIG. 4 is a block diagram illustrating a configuration of the trainer-side terminal corresponding to at least one of the embodiments of the present invention.

FIG. 4 is a block diagram illustrating a configuration of the trainer-side terminal corresponding to at least one of the embodiments of the present invention. The trainer-side terminal 4 includes at least a controller 41, a RAM 42, a storage 43, a sound processor 44, a sensor unit 46, a graphics processor 48, a display unit 49, a communication interface 50, an interface unit 51, and a camera unit 53, and each of those is connected via an internal bus.

The controller 41 is configured with a CPU and a ROM, and includes an internal timer for clocking the time. The controller 41 executes programs stored in the storage 43 and controls the trainer-side terminal 4. The RAM 42 is a work area of the controller 41. The storage 43 is a memory area for saving programs and data.

The controller 41 reads out the program and data from the RAM 42 and performs processing. The controller 41 processes the program and the data loaded on the RAM 42 to output an instruction to output sound to the sound processor 44 and to output an image drawing command to the graphics processor 48.

The sound processor 44 is connected to a sound output apparatus 45 that is a speaker. When the controller 41 outputs an instruction of sound output to the sound processor 44, the sound processor 44 outputs a sound signal to the sound output apparatus 45.

The sensor unit 46 includes at least one or more sensor selected from a group consisting of a depth sensor, an accelerometer, a gyro sensor, a GPS sensor, a fingerprint authentication sensor, a proximity sensor, a magnetic sensor, a luminance sensor, a GPS sensor, and a barometric pressure sensor. In view of monitoring in detail the state of the exercise performed by the client, it is preferable for the sensor unit 46 to include the depth sensor, for example. Note that, in order to monitor in detail the state of the exercise performed by the client, an external apparatus such as a motion capture apparatus, a pressure sensor, electromyography, or an ultrasonic measurement device may be used, and the information from the external apparatus may be received at the trainer-side terminal 4.

The graphics processor 48 is connected to the display unit 49. The display unit 49 includes a display screen 49a and a touch input unit 49b. When the controller 41 outputs an image drawing command to the graphics processor 48, the graphics processor 48 develops an image on a frame memory 47, and outputs a video signal for displaying the image on the display screen 49a. The touch input unit 49b receives operation input of the trainer, senses a pressure on the touch input unit 49b applied by a finger, a stylus, or the like and shift of the position of the finger or the like, and detects a change and the like of the coordinate position. The display screen 49a and the touch input unit 49b may also be configured integrally like a touch panel, for example.

The graphics processor 48 executes drawing of a single image by a frame unit. One frame time of the image is 1/30 seconds, for example. The graphics processor 48 has a role of dispersing the load of the entire system undertaking a part of calculation processing regarding drawing the image that is used to be carried out by the controller 41 alone.

The communication interface 50 is capable of connecting to the communication network 2 wirelessly or with wire, and capable of transmitting/receiving data via the communication network 2. The data received via the communication network 2 is loaded on the RAM 42, and calculation processing is performed by the controller 41.

An input unit 52 (for example, a mouse or a keyboard) can be connected to the interface unit 51. Input information inputted by the trainer through the input unit 52 is stored in the RAM 42, and the controller 41 executes various kinds of calculation processing based on the input information. Alternatively, it is also possible to connect a storage medium reader to the interface unit 51, and load the program, the data, and the like from an external memory or the like. Further, it is also possible to use the display unit 49 provided with a touch panel as the input unit 52.

The camera unit 53 is for capturing images of the client, and captures the postures of the client in a steady state and/or moving state and the state where the client is performing the exercise, for example. The image captured by the camera unit 53 is outputted to the graphics processor 48. Note that the camera unit 53 may not be provided to the trainer-side terminal 4. For example, the captured images of the client may be acquired by fetching images captured by an external image capturing apparatus.

Next, functions of the therapy and/or exercise instructing process management system corresponding to at least one of the embodiments of the present invention will be described. The system includes an input receiving function, an image capturing function, an object generating function, a posture assessing function, a muscle tone assessing function, a display function, a stage determining function, an exercise menu determining function, a transmitting function, a receiving function, and a storing function, for example.

The input receiving function is provided to both the client-side terminal 1 and the trainer-side terminal 4, and has a function of receiving operation input made on each terminal by the client or the trainer. The operation input may be done via an input apparatus such as a touch panel or a keyboard provided to each of the terminals, for example. The input receiving function receives input of information regarding the client such as the chief complaint of the client, the purpose of exercise, and the performed exercise, and information regarding communication between the client and the trainer, for example.

The image capturing function has a function of capturing images of the client. The image capturing function is preferable to be provided to at least either the client-side terminal 1 or the trainer-side terminal 4, and more preferable to be provided to the both. Note that, instead of the image capturing function, it is also possible to be configured to be capable of fetching the images captured by an external image capturing apparatus to each of the terminals.

The object generating function is a function that generates a prescribed object corresponding to a prescribed site of the client based on the captured image of the client in a steady state and/or a moving state. The generated object can be displayed on the display screen 19a and the display screen 49a. When the captured image is a video, for example, an object may be generated for each of frames constituting the video or an object may be generated only for a prescribed frame constituting the video, such as a still image acquired by temporarily stopping the video.

The posture assessing function has a function of assessing the posture of the client in a steady state and/or a moving state. The posture assessing function can assess the posture of the client based on the captured image of the posture of the client in a steady state and/or a moving state or an object generated by the object generation function, for example. The posture assessing function is preferable to have a function of automatically calculating which pattern the posture of the client belongs to among a plurality of posture patterns exhibiting differences with respect to an ideal posture that is set in advance.

The muscle tone assessing function has a function of surmising and deducing the muscle tone in a prescribed site of the client. The muscle tone assessing function surmises the muscle tone based on at least one out of the posture of the client in a steady state and/or a moving state, the object generated by the object generation function, and the pattern of the posture of the client, for example. The muscle tone assessing function can surmise whether the muscle tone of a prescribed site of the client is in a tensed (shortened) hypertonic state, in a relaxed (weakened) hypotonic state, or in a normal state. Note that the object generation function, the posture assessing function, and the muscle tone assessing function will be described in detail in latter paragraphs.

The display function is provided to both the client-side terminal 1 and the trainer-side terminal 4, and has a function of displaying a menu screen, an input receiving screen, information regarding the posture assessment, information regarding exercise menus, and various kinds of information such as posting content received by a posting receiving function to be described later, for example, in a mode that can be recognized by the client and the trainer.

The stage determining function has a function of determining the stage the client belongs to among the plurality of stages set in advance based on at least one out of the posture of the client in a steady state and/or a moving state, the object generated by the object generation function, and information regarding the client such as the chief complaint of the client and the purpose of the exercise. Note here that the "stages" are gradually classified phases of the state of the body of the client, and the criteria for classifying the stages can be set as appropriate.

Figure 5:
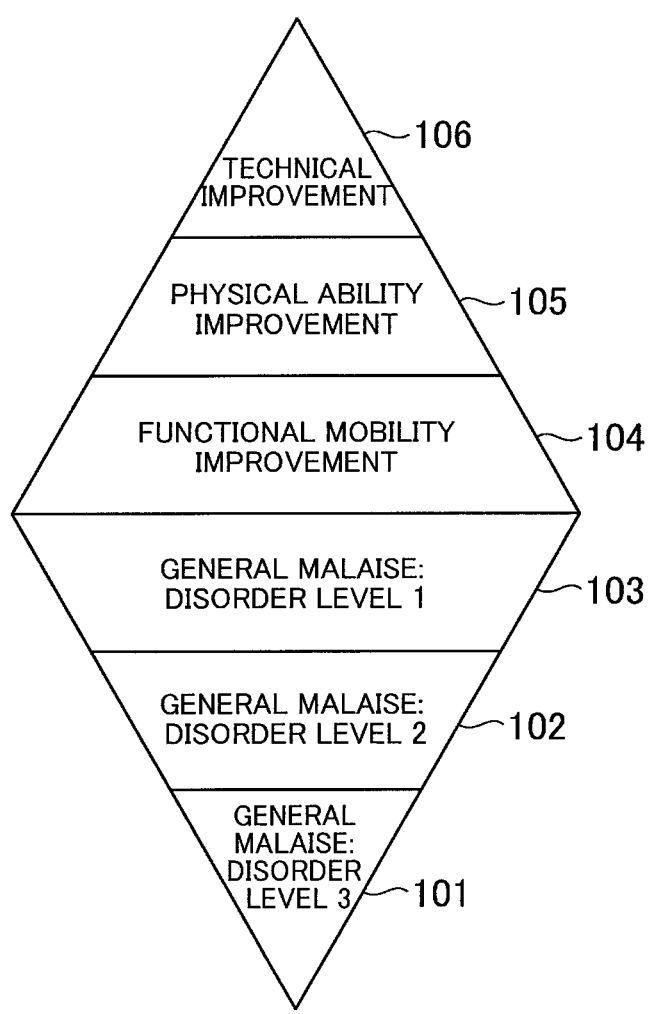
FIG. 5 is a diagram illustrating an example of stage classification corresponding to at least one of the embodiments of the present invention.

FIG. 5 is a diagram illustrating an example of stage classification corresponding to at least one of the embodiments of the present invention. In the example of FIG. 5, the state of the body of the client is classified into six stages 101 to 106, and the state moves up by one stage or more when a problem and a subject generated in each stage are overcome.

The stage 101 "general malaise: disorder level 3" is a state where there is pain constantly felt at least in a part of the body without moving the body. When classified in the stage 101, exercise is to be performed while controlling the symptom of the client by giving medicine and keeping the body at rest, for example, to achieve improvement. The stage 102 "general malaise: disorder level 2" is a state where there is pain felt a least in a part of the body while moving the body. When classified in the stage 102, the patient is considered to be in a state where physical strength is gradually decreasing. Therefore, exercise is to be performed while controlling the symptom of the client by giving physical therapy and keeping the part of the body at rest, for example, to achieve improvement.

The stage 103 "general malaise: disorder level 1" is a state where there is pain constantly felt at least in a part of the body after moving the body. When classified in the stage 103, it is considered that the functional mobility has failed (basic functions of the body have deteriorated). Therefore, after having the client perform appropriate exercise including exercise for improving the basic functions, for example, post-exercise aftercare such as a massage and stretching is performed to achieve improvement.

All of the stages 104 to 106 are states where it is possible to move without feeling pain in the body. The stage 104 "functional mobility improvement" is a stage aiming to improve the functional mobility by acquiring stability and cooperativeness of the whole body, for example. When classified in the stage 104, conditioning, treatment, and the like are performed to achieve improvement, for example.

The stage 105 "physical ability improvement" is a stage aiming to improve the physical ability such as the muscular strength, agility, and cardiopulmonary function by acquiring the body that can bear still higher load. When classified in the stage 105, fitness, training, and the like are performed to achieve improvement, for example. The stage 106 "technical improvement" is a stage aiming to improve the technique for aptly operating the body and the techniques of various kinds of sports and the like. When classified in the stage 106, training and practice of various kinds of sports as well as practicing ordinary life activities and the like are performed to achieve improvement, for example.

As described above, by gradually classifying the state of the body into the stages and determining the stage the client belongs to, the client can easily grasp the current state of the own body. Further, by enabling the client to set the target stage, it becomes possible for the client and the trainer to share the process to reach the target stage of the client, thereby making it possible to provide a highly satisfactory system for the both.

Returning to the functions of the system, the exercise menu determining function has a function of determining the exercise menu to be performed by the client based on the posture of the client in a steady state and/or moving state or based on the object generated by the object generation function. It is preferable for the exercise menu determining function to determine the exercise menu based further on the information regarding the client such as the chief complaint of the client and the purpose of exercise. Note that the exercise menu determining function may be the function that determines candidates of the exercise menu to be performed by the client. When configured as such, the trainer or the client may be allowed to select the exercise menu to be performed by the client from the candidates of the exercise menu, for example.

The transmitting function is provided to the client-side terminal 1, the server apparatus 3, and the trainer-side terminal 4. The transmitting function has a function of transmitting the information required for achieving the therapy and/or exercise instructing process management from the client-side terminal 1, the server apparatus 3, or the trainer-side terminal 4 as the origin to the client-side terminal 1, the server apparatus 3, or the trainer-side terminal 4 as the destination.

The receiving function is provided to the client-side terminal 1, the server apparatus 3, and the trainer-side terminal 4. The receiving function has a function of receiving the information required for achieving the therapy and/or exercise instructing process management from the client-side terminal 1, the server apparatus 3, or the trainer-side terminal 4 as the origin.

The storing function has a function of storing at least the information regarding assessment of the posture acquired by the posture assessing function and the information regarding the exercise menu performed by the client, which is the exercise menu determined by the exercise menu determining function. Further, the storing function is preferable to store the information regarding the assessment of the posture and the information regarding the exercise menu performed by the client in association with the date or the time and date on which those are performed. Furthermore, it is preferable for the storing function to be able to store the information and the like received via input of the input receiving function, for example, and also preferable to be able to store such information in association with the date or the time and date on which the information is inputted or the information is transmitted. While the storing function simply needs to be provided to at least one or more out of the client-side terminal 1, the server apparatus 3, and the trainer-side terminal 4, it is preferable to be provided to at least the server apparatus 3.

While the object generating function, the posture assessing function, the muscle tone assessing function, the stage determining function, and the exercise menu determining function may simply be provided to at least one out of the client-side terminal 1, the server apparatus 3, and the trainer-side terminal 4, it is preferable to be provided to at least the trainer-side terminal 4, and more preferable to be provided to the client-side terminal 1 and the trainer-side terminal 4.

Figure 6:
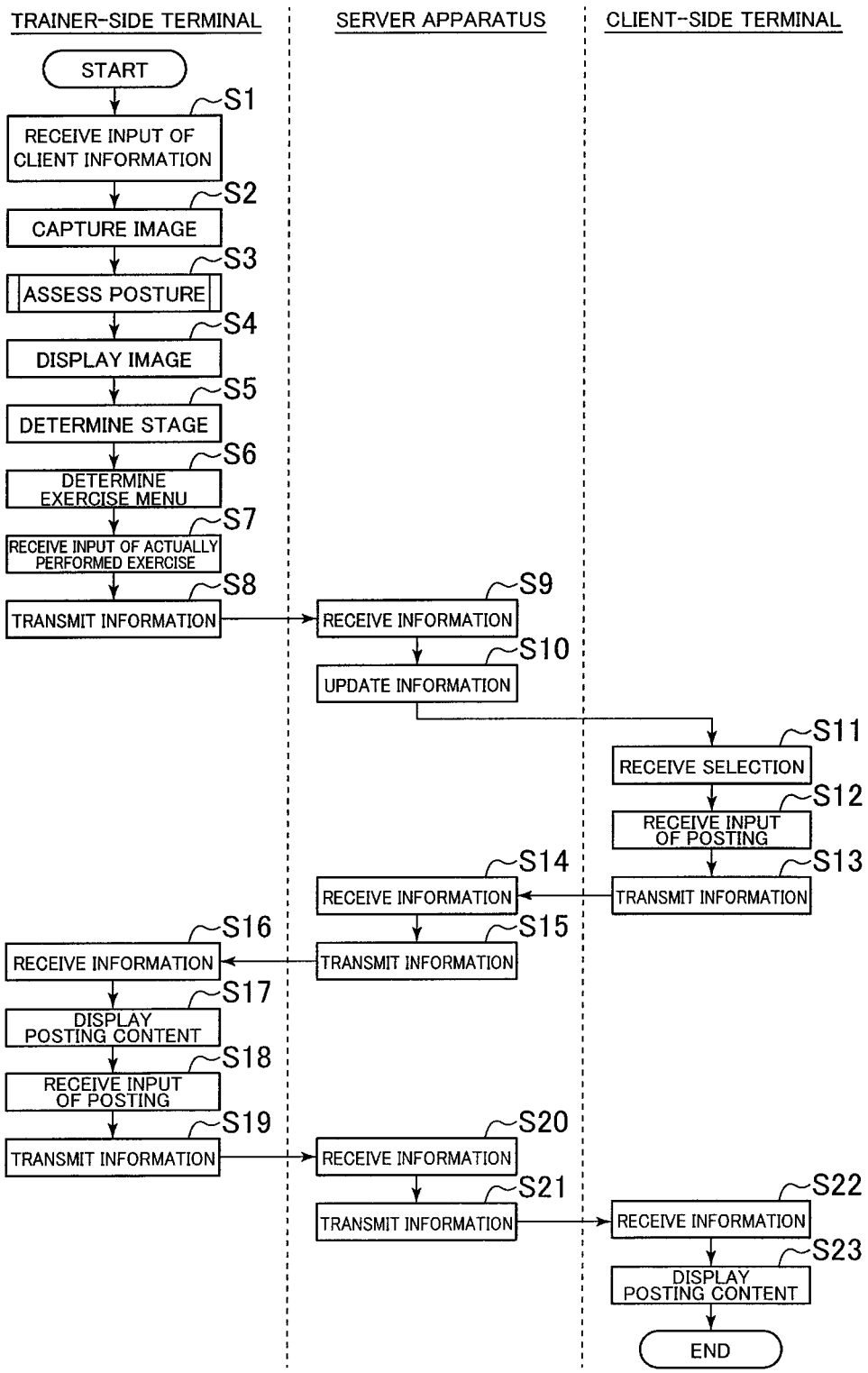
FIG. 6 is a flowchart of the therapy and/or exercise instructing process management processing corresponding to at least one of the embodiments of the present invention.

Next, therapy and/or exercise instructing management processing according to the embodiment will be described. FIG. 6 is a flowchart of the therapy and/or exercise instructing process management processing corresponding to at least one of the embodiments of the present invention.

As a premise of the first embodiment, an application for utilizing the system according to the first embodiment is installed in the client-side terminal 1 and the trainer-side terminal 4, for example. When the application is started in the client-side terminal 1, use of the application is permitted on condition that information regarding an account, a password, and the like of the client set in advance or identification information of the client-side terminal 1 acquired at the time of startup is transmitted to the server apparatus 3 and authenticated, for example, thereby making it possible to read and use the information associated with the client stored in the server apparatus 3.

Further, when application is started in the trainer-side terminal 4, use of the application is permitted on condition that information regarding an account, a password, and the like of the trainer set in advance or identification information of the trainer-side terminal 4 acquired at the time of startup is transmitted to the server apparatus 3 and authenticated, for example, thereby making it possible to read and use the information associated with the trainer stored in the server apparatus 3. The information associated with the trainer includes information regarding a plurality of clients to whom the trainer gives exercise instructions, for example. Note that it is also possible to cancel the association between the trainer information and the client information in response to a request from the trainer-side terminal 4 or the client-side terminal 1, and to associate the client information with trainer information of another trainer, for example.

The trainer selects a client to give an exercise instruction from now on from the information displayed on the trainer-side terminal 4 regarding a plurality of clients to whom the trainer gives exercise instructions. When the client to give the exercise instruction from now on is a person who uses the system for the first time, registration processing for registering the client as the user of the system is performed in the client-side terminal 1 or the trainer-side terminal 4, for example. In the registration processing, input of the information regarding the name, gender, age, life style, exercise habits, symptoms, and purpose of exercise of the client, for example, is received, and the received information is stored in the server apparatus 3. Hereinafter, mainly the case of giving an exercise instruction to the client who has already used the system will be described.

First, input of the information regarding the client is received in the trainer-side terminal 4 (step S1). The information regarding the client to be inputted is the information regarding the body condition of the client such as the chief complaint of the client and pain or a sense of discomfort, for example. When there is no change in the body condition and the like of the client from that of the previous instruction, step S1 may be omitted.

Figure 7:
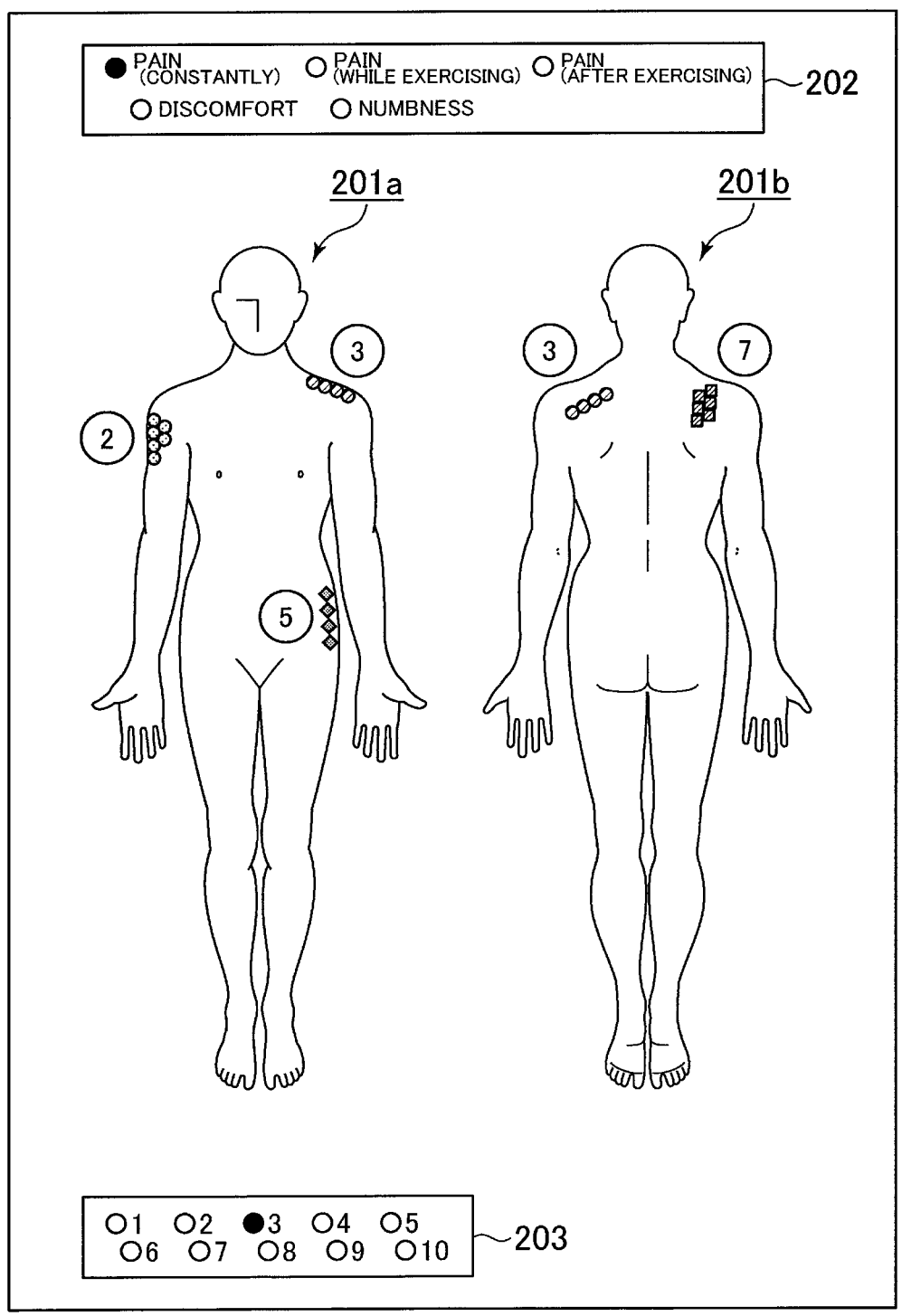
FIG. 7 is an example of a display screen for inputting the information regarding the body condition of the client, which corresponds to at least one of the embodiments of the present invention.

FIG. 7 is an example of a display screen for inputting the information regarding the body condition of the client, which corresponds to at least one of the embodiments of the present invention. On the display screen of the trainer-side terminal 4, body schematic images 201a, 201b, a symptom selection section 202, and a symptom level selection section 203 are displayed. The trainer inputs the types of the symptoms generated in the client, the sites where the symptoms are present, and the levels of the symptoms in the sites based on the result of an interview with the client.

The body schematic image 201a is a schematic view showing a front-side body, and the body schematic image 201b is a schematic view showing a back-side body. The symptom selection section 202 is a section for selecting the types of the symptoms generated in the body. While examples of the types of the symptoms displayed in the symptom selection section 202 may be "pain (constantly)", "pain (while exercising)", "pain (after exercising), "discomfort", and "numbness", the types are not limited to those.

Further, for each of the symptoms displayed in the symptom selection section 202, a marker corresponding to each of those is set. Each of the markers is preferable to be different in colors, patterns, or the like. For example, when the trainer selects "pain (constantly)" from the symptom selection section 202 and touches the left shoulder part of the body schematic image 201a, the marker corresponding to "pain (constantly)" is displayed on the touch-operated part. Such configuration makes it possible to easily grasp the type of the symptom generated in the client and the site where the symptom is generated. Further, by employing a configuration to change the color density of the marker in accordance with the number of touch-operations, the level of the symptom can be easily grasped as well in addition to the type of the symptom generated in the client and the site where the symptom is generated. Furthermore, it is preferable to be able to numerically express the level of the symptom based on the color density.

The symptom level selection section 203 is the section for selecting the levels of various kinds of symptoms such as the pain and a sense of discomfort. The levels of the various kinds of symptoms can be assessed by using a scale such as NRS (Numerical Rating Scale), VRS (Verbal Rating Scale), or FPS (Face Pain Scale), for example. In the example of FIG. 7, NRS is used. NRS is a method that sets the state having no symptom (pain) at all as "0" and the state having the worst pain that can be imagined as "10", and assesses the levels of the symptoms in eleven stages from 0 to 10. When the level of the symptom is "0", input is unnecessary. Therefore, numerals from 1 to 10 are displayed in the symptom level selection section 201.

For example, when the trainer selects "3" from the symptom level selection section 203 and touches the left shoulder part of the body schematic image 201a, a numeral "3" is displayed in the vicinity of the left shoulder part in the body schematic image 201a. With such configuration, it becomes possible to easily grasp the levels of the symptoms generated in the client.

Returning to the flowchart of FIG. 6, the trainer-side terminal 4 captures the image of the posture of the client in a steady state and/or a moving state (step S2). As the steady state, for example, a state keeping a posture such as a standing position, a bent-forward position while standing, a bent-backward position while standing, a rotating position while standing, a sitting position, a knee-standing position, or the like is preferable. However, the steady state is not limited to those. Further, as the moving state, for example, it is preferable to be a state where a multi-joint exercise is performed with no shift in the base of support. Specifically, overhead squat, single-leg squat, squat and hip rotation, bending forward while standing, bending backward while standing, rotating while standing, shoulder abduction, shoulder horizontal adduction, or the like is preferable. However, the moving state is not limited to those. In view of increasing the easiness and accuracy of the assessment, it is preferable to have the client perform at least one out of the standing position, the overhead squat, and the squat and hip rotation in step S2, and to capture the image of the posture of the client.

Further, the posture in step S2 may be the posture in a state where the client is on a prescribed exercise aid. As the exercise aid, it is preferable to use a substantially columnar aid or a substantially semicolumnar aid. Specifically, examples thereof may be StretchPole® and StretchPole® HALF CUT manufactured by LPN.Corporation. When such exercise aids are used in step S2, it is preferable to capture images of the postures in a state where a spine position is kept on the exercise aid, in a state when performing axial rotation while taking a spine position on the exercise aid, and in a state when elevating arms and legs by taking a spine position or a prone position on the exercise aid, for example.

Further, as the exercise aid, it is preferable to have an abdomen support part that supports the abdomen of the client and to have a protruded part provided on a side opposing to the side of the abdomen support part supporting the abdomen for enabling the exercise of moving laterally while supporting the abdomen, and preferable to be able to support the abdomen of the client when the client takes a prone position and to enable the client to move limbs in that state. Specifically, examples thereof may be SWING STRETCH® and the like manufactured by LPN.Corporation. When such exercise aid is used in step S2, it is preferable to capture an image of the posture when lifting a hand and a leg at diagonal positions from the floor, for example, from a state where both elbows and both knees are placed on the floor by while taking a prone position on the exercise aid, for example.

Further, the images are captured from the front of the client, from the side, or from the two directions that are from the front and the side depending on the contents to be performed by the client. For example, it is preferable to capture the images from the two directions that are from the front and the side in a case of a standing position and a case of overhead squat, while it is preferable to capture the images from the front in a case of squat and hip rotation. By changing the directions for capturing the images depending on the contents to be performed by the client, a more accurate posture assessment can be achieved.

Figure 8:
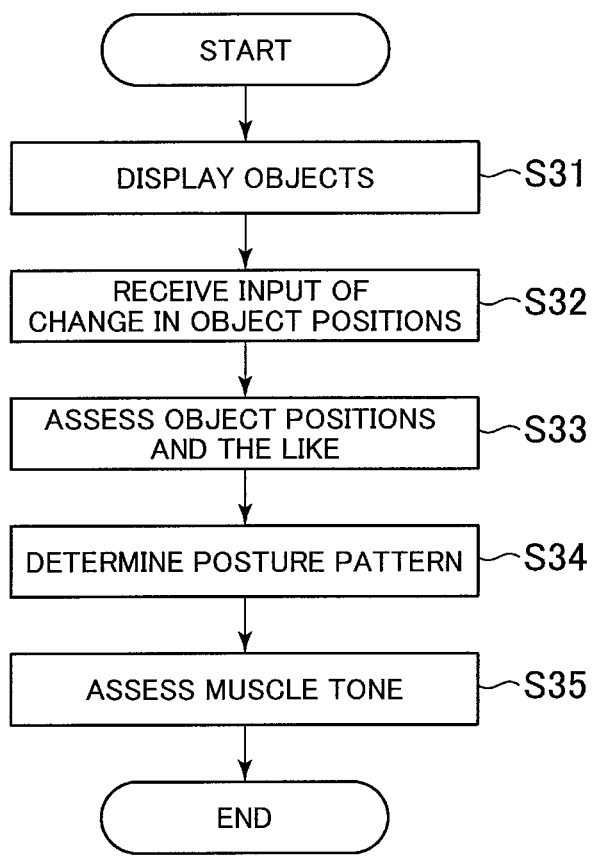
FIG. 8 is a flowchart of processing regarding the posture assessment that corresponds to at least one of the embodiments of the present invention.

Then, the trainer-side terminal 4 assess the posture of the client in a steady state and/or a moving state based on the images captured in step S2 (step S3). Here, the assessment of the posture performed in step S3 will be described in detail by using FIG. 8. FIG. 8 is a flowchart of processing regarding the posture assessment that corresponds to at least one of the embodiments of the present invention.

First, the trainer-side terminal 4 generates prescribed objects corresponding to each of prescribed sites of the body of the client based on the images captured in step S2, and integrally displays those while superimposing with the images captured in step S2 (step S31). Then, when the objects displayed in step S31 are not displayed at positions fully corresponding to the prescribed sites of the body of the client, the trainer-side terminal 4 receives input for changing the object positions from the trainer (step S32).

Figure 9A:
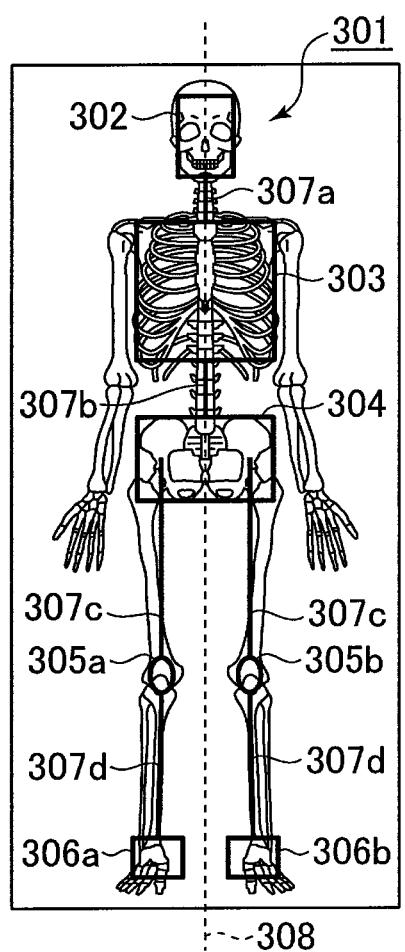
FIGS. 9A and 9B are schematic views regarding an object generating method corresponding to at least one of the embodiments of the present invention.

FIG. 9 are schematic views regarding an object generating method corresponding to at least one of the embodiments of the present invention. FIG. 9A shows, by using a human skeleton chart 301, an example of the object generating method when using an image of a state captured from the front in which a client stands upright at a prescribed position such that each of the second toes of both feet faces the front while being parallel to each other, and looks straight at a designated article placed at a level of eyesight (standing position).

On the human skeleton chart 301, shown are a head object 302, a thorax object 303, a pelvis object 304, knee objects 305, and foot objects 306, which correspond to prescribed sites of the human skeleton chart. Further, a plurality of connecting lines 307a to 307d connecting each of the objects and a centroidal line 308 are shown on the human skeleton chart 301.

The head object 302 is preferable to be formed by taking a line connecting the positions of the right and left external acoustic openings as a lateral reference line and a facial median line connecting the position of the middle of the forehead and the position of the nasal groove as a longitudinal reference line, and by translating each of the reference lines to fit the outer rim of the skull, for example. The thorax object 303 is preferable to be formed by taking a line connecting the positions of the right and left acromial processes as well as a line connecting the positions of the right and left costal arches as lateral lines, respectively, and a line connecting the position of the jugular notch of manubrium of sternum and the position of the xiphoid process as a longitudinal reference line, and by translating the longitudinal reference line to fit the outer rim of the costae, for example.

The pelvis object 304 is preferable to be formed by taking a line connecting the positions of the right and left iliac crests as a lateral reference line and a line connecting the position of the pubic symphysis and the position of the navel as a longitudinal reference line, and by translating each of the reference lines to fit the outer rim of the pelvis, for example. The right knee object 305a and the left knee object 305b are preferable to be formed to correspond to the positions and size of the knee joints (the center of the patella), for example.

The right foot object 306a and the left foot object 306b can be formed based on the entire outer rim of the foot, for example, and, specifically, are preferable to be formed based on a horizontal line passing the tip of the toe, a horizontal line passing the medial malleolus, a vertical line passing the medial malleolus, and a vertical line passing the outer edge of the metatarsophalangeal joint. The connecting lines 307 connect the neighboring objects for visualizing the state and the like of the bones between the neighboring objects. The centroidal line 308 is preferable to be a line that passes the midpoint of a segment connecting the respective center points of the foot objects 306a and 306b, and is perpendicular to the floor face, for example.

The connecting lines 307 connect the neighboring objects for visualizing the state and the like of the bones between the neighboring objects. For example, it is preferable to form the connecting line 307a to correspond to the cervical vertebrae, the connecting line 307b to correspond to the lumbar vertebrae, the connecting lines 307c to correspond to the femurs, and the connecting lines 307d to correspond to the shinbones.

Note that each of the objects is generated for making it easier to visually grasp the positions and inclinations of each body site. Therefore, even though without the objects are not generated, it is also possible to perform an assessment of the posture based on the reference points and reference lines used for generating the above-described objects. Further, the shapes of the objects are not limited to the square shape and round shape shown in FIG. 9, but any shapes may be used as long as the positions and inclinations of each body site can be visually grasped therewith.

Figure 9B:
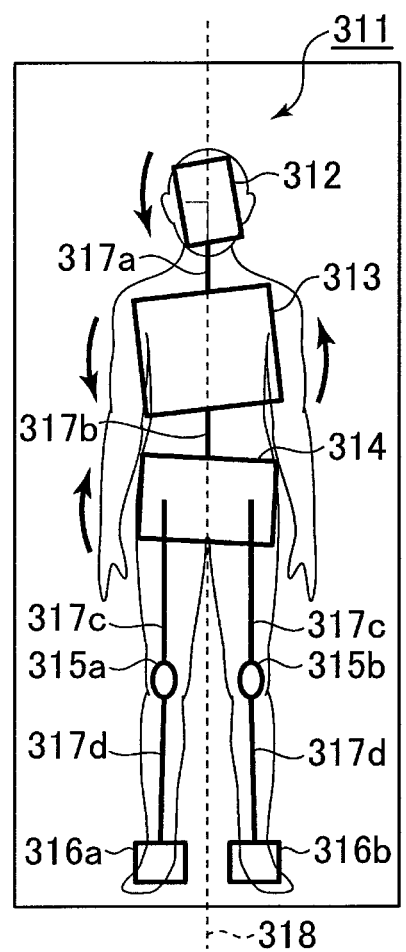

FIG. 9B is an example of display where prescribed objects are generated based on the posture image acquired by capturing the standing posture from the front, and the prescribed objects are superimposed on the posture image. On the posture image 311, shown are a head object 312, a thorax object 313, a pelvis object 314, knee objects 315, and foot objects 316 which are corresponding to prescribed sites of the body of the client. Further, a plurality of connecting lines 317a to 317d connecting each of the objects and a centroidal line 318 are shown on the posture image 311. Note that arrows shown in the drawing are displayed for making it easier to grasp the inclinations of each of the objects.

In FIG. 9B, each of the objects and the like is formed by using the method described in FIG. 9A. Each of the objects is preferable to be formed by the trainer-side terminal 4 by using a technique regarding conventionally known motion capture and a technique regarding image recognition, for example. When using the motion capture, each of the objects and the like can be formed by placing markers at the positions as the origins of the reference lines for forming each of the objects described above and detecting the positions of the markers, for example.

Further, at the time of capturing the image in step S2, it is also possible to display a reference image to be a reference for generating the objects such as the human skeleton chart shown in FIG. 9A on the display screen, for example, and capture the image by aligning the position of the body of the client with the reference image so as to display each of the objects formed based on the reference image while superimposing on the posture image.

When the positions and sizes of the generated objects and the like are inconsistent with those of the posture image, it is possible to receive input from the trainer and adjust the positions, sizes, and inclinations of the objects and the like, for example.

When the image captured in step S2 is a video, that is, when the assessment target is a posture of the client in a moving state, it is preferable to generate the objects based on a still image acquired by temporarily stopping the video in a prescribed frame to be assessed. The object generating method may be the same method as described above or may be a method according to the criterion set for each motion. In view of increasing the accuracy of the assessment made with the objects, motions performed in step S2 are preferable to be motions that include no changes in the shape of the spinal column and the body during the motions, such as flexion, extension, and rotation. However, the motions are not limited thereto. Examples of the motions that include no changes in the shape of the spinal column and the body during the motions, such as flexion, extension, and rotation, may be overhead squat, single-leg squat, and squat and hip rotation.

Returning to the flowchart of FIG. 8, the trainer-side terminal 4 assesses the positions and the like of the objects (step S33). In step S33, it is preferable to assess at least one or more out of the positions of each of the objects, inclinations, and the positional relationships between the neighboring objects, for example. Further, in view of performing a more accurate assessment on the posture of the client, it is more preferable to assess all of the positions and inclinations of each of the objects and the positional relationships between the neighboring objects.

It is preferable to assess the position of each of the objects based on the distance between the center of gravity of each of the objects and the distance to the centroidal line 318, for example. It is preferable to assess the inclination of each of the objects based on whether or not the lateral lines configuring each of the objects are parallel to the floor face (whether or not the object is inclined either to the right or left), for example. When the distance between the center of gravity of the object and the centroidal line 318 is zero or equal to or less than a prescribed distance, it is assessed that the position of the object is normal. Further, when the lateral lines configuring the object are substantially parallel to the floor face, it is assessed that the inclination of the object is normal.

It is preferable to assess the positional relationship between the neighboring objects based on how much shift there is in the distance between the prescribed references (for example, prescribed vertexes of the objects) of each of the objects, in the relation of the inclinations between each of the objects, and the like with respect to the case where the positions and the inclinations of each of the objects are normal.

Then, the trainer-side terminal 4 determines the posture pattern of the client from the plurality of posture patterns set in advance based on the assessment result of the objects acquired in step S33 (step S34). In step S34, it is preferable to select a feature exhibited in the posture of the client from a plurality of feature candidates set in advance based on the assessment result of the objects acquired in step S33, and to determine the posture pattern based on the selected feature, for example.

Note that the posture pattern is classified based on types of the postures often observed in general in a prescribed steady state or moving state, for example. The posture pattern is preferable to be set for each type of assessment targets, such as front standing posture, side standing posture, front overhead squat posture, side overhead squat posture, and the like. Note that the feature and/or the posture pattern determined in step S34 are preferable to be used for determining the exercise menu in step S6 to be described later, for example.

Note that the assessment of the positions and the like of the objects in step S33 and determination of the features and posture patterns in step S34 may be automatically performed by the trainer-side terminal 4 or may be performed by the trainer by assessing the positions and the like of the objects and selecting and inputting the feature observed in the posture of the client and the posture pattern thereof to the trainer-side terminal 4.

Figure 10:
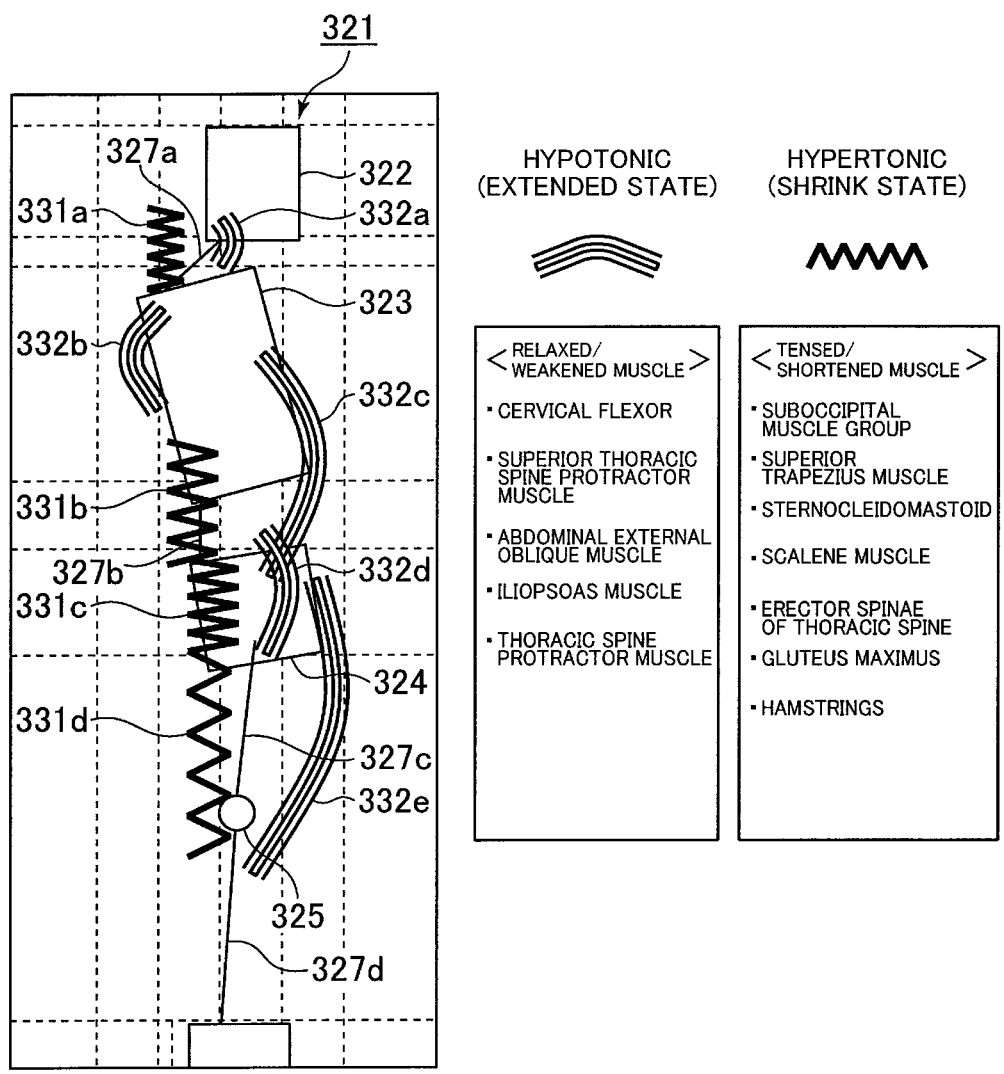
FIG. 10 is a schematic view regarding the assessment of the muscle tone corresponding to at least one of the embodiments of the present invention.

Further, the trainer-side terminal 4 surmises the muscle tone of the client based on the assessment result acquired in step S33 (step S35). FIG. 10 is a schematic view regarding the assessment of the muscle tone corresponding to at least one of the embodiments of the present invention. In the example of FIG. 10, shown is the assessment of the muscle tone when using an object image generated based on the image acquired by capturing a standing posture from the right side.

An object image 321 is configured with a head object 322, a thorax object 323, a pelvis object 324, a knee object 325, a foot object 326, and a plurality of connecting lines 327a to 327d. Markers 331a to 331d show the positions of muscles in a tensed (shortened) state (hereinafter, also referred to as "tensed muscles"). Markers 332a to 332e show the positions of muscles in a relaxed (weakened) state (hereinafter, also referred to as "relaxed muscles"). Specific examples of the tensed muscle indicated by the markers 331a to 331d and the relaxed muscles indicated by the markers 332a to 332e are shown in FIG. 10. Although not shown, when a centroidal line is to be displayed, it is preferable to define a vertical line drawn from about 2 cm front of the lateral malleolus to the floor face as the centroidal line.

The muscle at the position corresponding to the marker 331a is surmised as a tensed muscle based on the fact that the acute angle formed between the connecting line 327 and the upper side of the thorax object 323 is smaller than the case where the positions and inclinations of each of the objects are normal, for example. Further, the muscle at the position corresponding to the marker 332a is surmised as a relaxed muscle based on the fact that the obtuse angle formed between the connecting line 327 and the lower side of the head object 322 is larger than that of the case where the positions and inclinations of each of the objects are normal, for example.

Moreover, the muscle at the position corresponding to the marker 332c is surmised as a relaxed muscle based on the fact that the distance of a route from the position of the midpoint of the right side of the thorax object 323 to the vertex at the upper right side of the pelvis object 324 via the right side of the thorax object 323 is longer than that of the case where the positions and inclinations of each of the objects are normal, for example.

As described above, it is possible to surmise the muscle tone by assessing prescribed muscle assessment items such as the angles formed between the objects, the connecting lines, and the like, the direct distance or the route distance between prescribed reference points on the objects and the connecting lines, for example, based on the prescribed muscle assessment criterion set for each of the muscle assessment items.

Note that the surmise of the muscle tone in step S35 may be automatically performed by the trainer-side terminal 4 or may be performed by the trainer by assessing the prescribed muscle assessment items based on the prescribed muscle assessment criterion and inputting the information regarding the tensed muscles or the relaxed muscles to the trainer-side terminal 4. Further, it is also possible to associate each of the posture patterns with the surmised results of the muscle tone in each of the posture patterns and store those in advance. With such configuration, by simply determining the posture pattern of the client, for example, the surmised result of the muscle tone corresponding to such posture pattern can be acquired. Therefore, it is possible to lighten the processing load.

Note that the muscle tone surmised in step S35 is preferable to be presented to the client by using the image as shown in FIG. 10 where the object image and the markers are integrally displayed. With such configuration, the client can easily grasp the condition of the own body.

Further, the surmised result of the muscle state is preferable to be used for determining the exercise menu in step S6 to be described later, for example. Specifically, it is preferable to select the exercise menu for relaxing the tensed muscles and strengthening the relaxed muscles.

Figure 11:
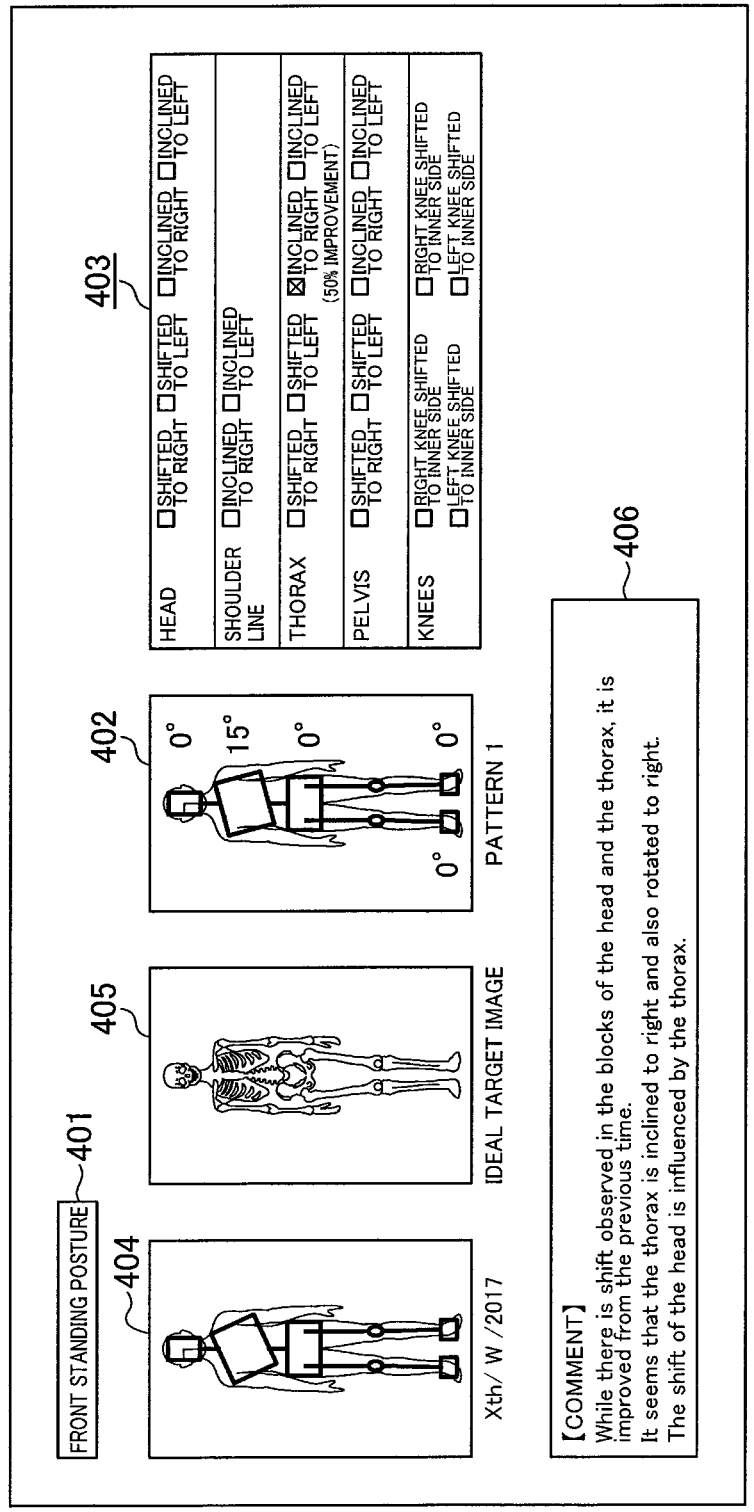
FIG. 11 is an example of the display screen displaying the image regarding the posture assessment that corresponds to at least one of the embodiments of the present invention.

Returning to the flowchart of FIG. 6, the trainer-side terminal 4 displays the image regarding the posture assessment made in step S3 (step S4). FIG. 11 is an example of the display screen displaying the image regarding the posture assessment that corresponds to at least one of the embodiments of the present invention. On the display screen of the trainer-side terminal 4, displayed are a posture type display section 401, a current image display section 402, a feature display section 403, a past image display section 404, an ideal target image/unideal target image display section 405, and a comment section 406.

The posture type display section 401 is a section that displays the type of the posture as the assessment subject. In the example of FIG. 11, it is displayed as "front standing posture" and an image acquired by capturing a standing position from the front is the assessment subject. It is preferable for the posture type display section 401 to be able to change to other posture types by receiving input of touch operations, for example.

The current image display section 402 is a section that displays a current image regarding the current posture of the client assessed in step S3. As the current image, it is preferable to be an image captured in step S2, an image of prescribed objects generated based on the image captured in step S2, or an image that integrally shows the image captured in step S2 and the prescribed objects generated based on the image, for example. In the example of FIG. 11, displayed in the current image display section 402 is the image that integrally shows the image captured in step S2 and the prescribed objects generated based on the image, and further displayed in the vicinity of each of the objects are inclination angles of each of the objects. With such configuration, the trainer and the client can easily grasp the current condition of the body of the client. Further, in the bottom of the current image display section 402, the posture pattern of the client determined in step 34 is displayed.

In the feature display section 403, features observed in the current posture of the client are displayed. The features displayed in the feature display section 403 are the features determined in step S34, for example. In the example of FIG. 11, the check box of "inclined to right" for the thorax is checked, which indicates that the thorax is inclined to the right direction in the current image displayed in the current image display section 402. Further, "(50% improvement)" is displayed under the check box of "inclined to right" for the thorax, which indicates the extent of the improvement made from the exercise instruction of the past such as the previous time or the first time. The extent of the improvement is preferable to be calculated by the trainer-side terminal 4 by comparing the information regarding the past and current postures, but may also be inputted by the trainer. By displaying the extent of the improvement, the client can easily feel the effect of the exercise instruction, thereby making it possible to give motivation to continuously receive the exercise instruction.

The past image display section 404 is a section that displays a past image regarding the posture of the client captured in the past. As the past image, it is preferable to be a posture image of the client captured in the past, an image of prescribed objects generated based on the posture image of the client captured in the past, or an image that integrally shows the posture image of the client captured in the past and the prescribed objects generated based on the image. In the vicinity of the past image display section 404, it is preferable to display the date on which the image displayed in the past image display section 404 is captured. In the example of FIG. 10, the date on which the image was captured is displayed as "W Xth, 2017" in the bottom of the past image display section 404.

Further, the most recent past image may be displayed in the past image display section 404, for example, or a past image of an any date desired by the trainer or the client may be displayed by receiving input of touch operations and the like. With the display in a mode capable of comparing the current image and the past image, the client can easily grasp the extent of the improvement in the posture. Note that the information for displaying the past image is acquired from the storage of the trainer-side terminal 4 or the server apparatus 3.

Further, in view of enabling the client to more easily grasp the extent of the improvement of the posture, it is preferable to generate and display an integrated image in which the past image and the current image are superimposed, for example. Specifically, it is preferable to generate and display an image in which the image of the prescribed objects generated based on the image captured in step S2 and the image of the prescribed objects generated based on the posture image of the client captured in the past are superimposed such that prescribed reference points thereof (for example, the centroidal lines) are aligned. With such configuration, changes between the objects in the current image and the objects in the past image can be easily grasped. As a result, the client can more easily grasp the extent of the improvement in the posture.

The ideal target image/unideal target image display section 405 is a section that displays an ideal target image showing the posture to be the target of the client corresponding to the type of the posture displayed in the posture type display section 401 or an unideal target image showing the posture that is not supposed to be the target of the client, having in common at least a part of factors not satisfying the prescribed assessment criterion in the posture of the client. A specific example of the unideal target image may be an image that clearly shows the features in the posture pattern of the client determined in step S34. Note that the information for displaying the ideal target image or the unideal target image is acquired from the storage of the trainer-side terminal 4 or the server apparatus 3.

The image to be displayed in the ideal target image/unideal target image display section 405 is preferable to be selectable by the trainer through input of touch operations and the like made on the trainer-side terminal 4, for example. With the display in a mode capable of comparing the current image with the ideal target image or the unideal target image, the client can easily grasp in what respect the current posture of the client has a problem. Further, in view of enabling the client to more easily grasp in what respect the current posture of the client has a problem, it is preferable to generate and display an integrated image in which the current image and the ideal target image or the unideal target image are superimposed, for example. Specifically, it is preferable to employ a configuration similar to the mode that is described above regarding the past image display section 404.

The comment section 406 is a section that displays a comment regarding the assessment of the current posture of the client. The comment displayed in the comment section 406 may be automatically generated by the trainer-side terminal 4 based on the assessment result acquired in step S3 or may be inputted by the trainer. By displaying the comment regarding the assessment of the posture, the client can easily grasp in what respect the current posture of the client has a problem.

Returning to the flowchart of FIG. 6, the trainer-side terminal 4 determines the current stage of the client based on the result of the posture assessment made in step S3 and the information regarding the body condition of the client inputted in step S1 (step S5). It is preferable to select the stage of the client from a plurality of stages as shown in FIG. 5, for example.

Then, the trainer-side terminal 4 determines the exercise menu to be performed by the client based on at least one or more out of the information regarding the body condition of the client inputted in step S1, the posture pattern determined in step S34, and the surmised result of the muscle tone acquired in step S35 (step S6). In view of determining the exercise menu more suitable for the client, it is preferable in step S6 to determine the exercise menu based on the information regarding the body condition of the client and the posture pattern, for example, and more preferable to determine the exercise menu based on the information regarding the body condition of the client, the posture pattern, and the surmised result of the muscle tone.

FIG. 12 is an example of a master table that corresponds to at least one of the embodiments of the present invention. In step S6, the exercise menu to be performed by the client is determined by referring to the master table as shown in FIG. 6, for example.

In a master table 501, the information of the client inputted in step S1 such as symptom site 502, symptom type 503, and symptom level 504, posture pattern 505 determined in step S34 and exercise menu 506 to be performed by the client are stored in an associated manner.

For example, when there is no symptom inputted in step S1 and the posture pattern 505 determined in step S34 is "pattern A-1", "exercise menu A1" is selected in step S6 as the exercise menu 506 to be performed by the client. Further, when there is no symptom inputted in step S1 and the posture pattern 505 determined in step S34 is "pattern B-1", for example, "exercise menu B1" is selected in step S6 as the exercise menu 506 to be performed by the client.

Note here that "pattern A-1" indicates a case where the posture image of the client assessed in step S3 is an image of a front standing posture and the posture pattern of the client determined in step S34 is "front standing posture: pattern 1", for example. Further, "pattern B-1" indicates a case where the posture image of the client assessed in step S3 is an image of an overhead squat posture captured from the front and the posture pattern of the client determined in step S34 is "overhead squat: pattern 1", for example.

Further, for example, in a case where there is a pain in the left shoulder part after exercise and it is inputted that the level of the pain is in a range of 1 to 3, and the posture pattern 505 determined in step S34 is "pattern A-1", "exercise menu A11" is selected in step S6 as the exercise menu 506 to be performed by the client. However, when the symptom is being suppressed by medication, physical therapy, or the like, "exercise menu A1" may also be selected as the exercise menu 506 to be performed by the client for improving the functional motions.

When the client has symptoms in a plurality of sites, a plurality of exercise menus may be selected based on all the symptoms, for example, and the exercise menu may also be determined based on the symptom of the highest symptom level. Further, it is also possible to set the priority among each of the symptoms, and determine the exercise menu based on the symptom of the highest priority.

Similarly, in a case where the posture patterns are determined for each of a plurality of types of postures in step S34, it is possible to select a plurality of exercise menus based on all the posture patterns or to determine the exercise menu based on a prescribed posture pattern such as a posture pattern that is assessed to be most different from a normal state, for example. Further, it is also possible to set the priority among each of the posture patterns, and determine the exercise menu based on the posture pattern of the highest priority.

The exercise menu includes at least one or more type of exercise, for example. Further, the exercise menu is preferable to include the number of times the exercise is to be done. The information regarding the exercise menu determined in step S6 is displayed on the trainer-side terminal 4. The information regarding the exercise menu to be displayed is preferable to include an image showing how to do the exercise, the purpose of the exercise, and the priority of the exercise, for example, in addition to the name of the exercise, and the number of times the exercise to be performed. Such configuration makes it easier to enable the client to appropriately perform the most effective exercise. In addition, as a result of understanding and becoming conscious about the purpose of the exercise, the effect of the exercise can be increased further.

From the exercise menu determined in step S6, the trainer determines the exercise to be performed by the client on the spot and the exercise to be performed by the client at home and the like by considering the priority and the like.

Returning to the flowchart of FIG. 6, the trainer-side terminal 4 receives input of the information regarding actual exercise such as the exercise menu the client actually performed on the spot and the number of times of the exercise actually performed out of the exercise menu determined in step S6 (step S7). Then, the trainer-side terminal 4 transmits the information regarding the actually performed exercise inputted in step S7 to the server apparatus 3 (step S8).

Note that the information regarding the client inputted in step S1, the information regarding the posture image of the client captured in step S2, the information regarding the assessment of the posture of the client assessed in step S3, the information regarding the stage to which the client belongs determined in step S5, and the information regarding the exercise menu determined in step S6 may be transmitted in step S8 to the server apparatus 3 along with the information regarding the actually performed exercise, or each thereof may be transmitted to the server apparatus 3 in the respective steps.

Further, each processing from step S1 to Step S8 is preferable to be executable also by the client-side terminal 1. With such configuration, it is possible to give a remote exercise instruction from the trainer to the client, for example. In addition, it becomes also possible to perform exercise process management only with the client-side terminal 1 and the server apparatus 3 without having a trainer, which is a modification example of the embodiment.

Further, each processing from step S3 to step S6 may be executed also in the server apparatus 3. With such configuration, the processing load imposed upon the trainer-side terminal 4 or the client-side terminal 1 can be lightened.

Then, the server apparatus 3 receives the information transmitted in step S8 (step S9). Then, the server apparatus 3 updates the information associated with the client stored in the storage of the server apparatus 3 based on the received information (step S10). Each processing from step S8 to step S10 is performed when the trainer gives an exercise instruction to the client face to face, for example.

Each processing from step S11 to step S23 described hereinafter is processing for a case where the client performs the exercise menu at a place away from the trainer (for example, at home of the client) after the trainer gives a face-to-face instruction to the client, for example. When an application is started in the client-side terminal 1 and authentication and the like by the server apparatus 3 are completed, the client-side terminal 1 becomes capable of using the system and the information associated with the client can be displayed on the client-side terminal 1, for example.

First, the client-side terminal 1 receives selection of a service the client desires from the service items that can be used by the client (step S11). While not limited thereto, examples of the service items to be selected may be viewing the information and the like regarding posture assessment, history of actually performed exercise, and instructing process, assessment of posture images captured at home, and communication with the trainer.

Note here that communication with the trainer is to mutually exchange the intention and information between the trainer and the client, for example. Specifically, examples thereof may be sending questions regarding the instructing process and the method for performing the exercise menu, viewing the answers to the questions, reporting the exercise menu performed by the client at home to the trainer, sending captured images of the state of the exercise performed by the client at home to the trainer, and viewing the assessment and advice from the trainer regarding the exercise to be performed at home or the performed exercise. However, the communication with the trainer is not limited to those.

When communication with the trainer is selected in step S11, the client-side terminal 1 receives input of a massage and/or an image (hereinafter, also referred to as "posting content") to be sent to the trainer (step S12). Then, the client-side terminal 1 transmits the information regarding the posting content inputted and received in step S12 to the server apparatus 3 (step S13).

Then, the server apparatus 3 receives the information transmitted in step S13 (step S14). The information received in step S14 is stored in the storage of the server apparatus 3 and, in response to a request from the client-side terminal 1 or the trainer-side terminal 4, transmitted to the requesting terminal.

Then, when there is a request from the trainer-side terminal 4, the server apparatus 3 transmits the information regarding the posting content stored in the storage to the trainer-side terminal 4 (step S15). Then, the trainer-side terminal 4 receives the information transmitted in step S15 (step S16). Thereafter, the trainer-side terminal 4 displays the posting content of the client based on the information received in step S16 (step S17).

Then, the trainer-side terminal 4 receives input of the posting content to be sent to the client (step S18). While not limited thereto, examples of the posting content in step S18 may be answers for the questions of the client, assessment and advice (for example, an image and the like showing a right exercise posture) for the exercise menu performed by the client at home, and instructions regarding the exercise menu to be performed by the client at home.

Then, the trainer-side terminal 4 transmits the information regarding the posting content inputted and received in step S18 to the server apparatus 3 (step S19). Then, the server apparatus 3 receives the information transmitted in step S19 (step S20). The information received in step S20 is stored in the storage of the server apparatus 3 and, in response to a request from the client-side terminal 1 or the trainer-side terminal 4, transmitted to the requesting terminal.

Then, when there is a request from the client-side terminal 1, the server apparatus 3 transmits the information regarding the posting content stored in the storage to the client-side terminal 1 (step S22). Then, the client-side terminal 1 receives the information transmitted in step S22 (step S23). Thereafter, the client-side terminal 1 displays the posting content of the trainer based on the information received in step S23 (step S17), and ends the process.

In step S17 and step S23, in view of improving perspicuity of the posting content and making it easier to grasp the circumstances of posting, it is preferable to display both the posting content of the trainer and the posting content of the client along the time series such as the time and date of the posting.

By having the steps from S12 to S23, the trainer can be fully involved in the exercise performed by the client at home, which is conventionally out of sight of the trainer, for example. Therefore, it is possible to improve the quality of the exercise of the client, thereby making it easier to improve the state of the body of the client. Further, it becomes also possible to decrease the possibility of having a discrepancy and the like generated in recognition of the client and the trainer, and to allow the both to fully share the instructing process from the current state of the client until reaching the target.

REFERENCE SIGNS LIST

1 CLIENT-SIDE TERMINAL
2 COMMUNICATION NETWORK
3 SERVER APPARATUS
4 TRAINER-SIDE TERMINAL
11 CONTROLLER
12 RAM
13 STORAGE
14 SOUND PROCESSOR
15 SOUND OUTPUT APPARATUS
16 SENSOR UNIT
17 FRAME MEMORY
18 GRAPHICS PROCESSOR
19 DISPLAY UNIT
20 COMMUNICATION INTERFACE
21 INTERFACE UNIT
22 INPUT UNIT
23 CAMERA UNIT
31 CONTROLLER
32 RAM
33 STORAGE
34 COMMUNICATION INTERFACE
41 CONTROLLER
42 RAM

43 STORAGE
44 SOUND PROCESSOR
45 SOUND OUTPUT APPARATUS
46 SENSOR UNIT
47 FRAME MEMORY
48 GRAPHICS PROCESSOR
49 DISPLAY UNIT
50 COMMUNICATION INTERFACE
51 INTERFACE UNIT
52 INPUT UNIT
53 CAMERA UNIT

The invention claimed is:

1. A therapy and/or exercise instructing process management system implemented by a client-side terminal operated by a client and a trainer-side terminal that is connectable to the client-side terminal via communication and operated by a trainer, the system comprising:
  an assessor that assesses a posture of the client in a steady state and/or a moving state;
  an exercise determiner that determines a type of exercise to be performed by the client based on an assessment made by the assessor considering the posture of the client; and
  a storage that stores information regarding the assessment made by the assessor and information regarding the exercise that is determined by the exercise determiner and performed by the client,
  wherein the assessor assesses whether a muscle tone of the client is in a tensed hypertonic state or in a relaxed hypotonic state based on a position of a prescribed body site of the client, an inclination of the prescribed body site of the client, and/or positional relationships among a plurality of the prescribed body sites in an image.

2. The therapy and/or exercise instructing process management system according to claim 1, further comprising:
  a displayer that is capable of displaying at least a part of the information stored in the storage on the client-side terminal and the trainer-side terminal.

3. The therapy and/or exercise instructing process management system according to claim 2,
  wherein the displayer further displays an ideal target image showing a posture to be a target of the client, the ideal target image corresponding to the posture of the client in the steady state and/or the moving state assessed by the assessor.

4. The therapy and/or exercise instructing process management system according to claim 2,
  wherein the displayer further displays an unideal target image showing a posture that is not supposed to be a target of the client, the unideal target image having in common at least a part of factors not satisfying a prescribed assessment criteria in the posture of the client, and corresponding to the posture of the client in the steady state and/or the moving state assessed by the assessor.

5. The therapy and/or exercise instructing process management system according to claim 2,
  wherein the storage stores the information regarding the assessment in association with date or time and date on which the assessment is made, and stores the information regarding the exercise performed by the client in association with date or time and date on which the exercise is performed; and
  the displayer is capable of displaying at least a part of the information stored in the storage in chronological order.

6. The therapy and/or exercise instructing process management system according to claim 2, further comprising:
  an inputter that inputs a site having a prescribed symptom in a body of the client, a type of the symptom of the site, and a level of the symptom of the site,
  wherein the displayer displays information indicating the type of the symptom of the site and the level of the symptom of the site at a position corresponding to the site having the prescribed symptom on a drawing regarding an external appearance of the body.

7. The therapy and/or exercise instructing process management system according to claim 2, further comprising:
  a posting receiver that receives a posting of a message and/or an image from the client-side terminal and the trainer-side terminal,
  wherein the displayer further displays the message and/or the image received by the posting receiver on the client-side terminal and the trainer-side terminal.

8. The therapy and/or exercise instructing process management system according to claim 7, further comprising:
  an image capturer capable of capturing an image of the client,
  wherein the posting receiver is capable of receiving a posting of an image of the exercise that is performed by the client and captured by the image capturer.

9. The therapy and/or exercise instructing process management system according to claim 1, further comprising:
  an image capturer capable of capturing an image of the client,
  wherein the assessor assesses the posture of the client in the steady state and/or the moving state based on the image captured by the image capturer.

10. The therapy and/or exercise instructing process management system according to claim 9,
  wherein the assessor assesses the posture based on a position of a prescribed body site of the client, an inclination of the prescribed body site of the client, and/or positional relationships among a plurality of prescribed body sites in the image captured by the image capturer.

11. The therapy and/or exercise instructing process management system according to claim 9, further comprising:
  an object drawer that draws a plurality of objects for visualizing positions and/or inclinations of each of prescribed body sites of the client in the image captured by the image capturer,
  wherein the assessor assesses the posture based on the positions of the objects, the inclinations of the prescribed body site of the client, and positional relationships among the plurality of objects.

12. A non-transitory computer-readable recording medium including a program causing a computer apparatus to execute therapy and/or exercise instructing process management, the program causing the computer apparatus to function as:
  an assessor that assesses a posture of a client in a steady state and/or a moving state;
  an exercise determiner that determines a type of exercise to be performed by the client based on an assessment made by the assessor considering the posture of the client; and
  a storage that stores information regarding the assessment made by the assessor and information regarding the exercise that is determined by the exercise determiner and performed by the client,
  wherein the assessor assesses whether a muscle tone of the client is in a tensed hypertonic state or in a relaxed hypotonic state based on a position of a prescribed body site of the client, an inclination of the prescribed body site of the client, and/or positional relationships among a plurality of the prescribed body sites in an image.

13. A computer apparatus executing therapy and/or exercise instructing process management, comprising:
    an assessor that assesses a posture of a client in a steady state and/or a moving state;
    an exercise determiner that determines a type of exercise to be performed by the client based on an assessment made by the assessor considering the posture of the client; and
    a storage that stores information regarding the assessment made by the assessor and information regarding the exercise that is determined by the exercise determiner and performed by the client,
    wherein the assessor assesses whether a muscle tone of the client is in a tensed hypertonic state or in a relaxed hypotonic state based on a position of a prescribed body site of the client, an inclination of the prescribed body site of the client, and/or positional relationships among a plurality of the prescribed body sites in an image.

14. A therapy and/or exercise instructing process management method, comprising:
    assessing a posture of a client in a steady state and/or a moving state;
    determining a type of exercise to be performed by the client based on an assessment made in the assessing considering the posture of the client; and
    storing, in a computer apparatus, information regarding the assessment made in the assessing and information regarding the exercise that is determined in the determining exercise and performed by the client,
    wherein the assessor assesses whether a muscle tone of the client is in a tensed hypertonic state or in a relaxed hypotonic state based on a position of a prescribed body site of the client, an inclination of the prescribed body site of the client, and/or positional relationships among a plurality of the prescribed body sites in an image.

* * * * *